(12) United States Patent
Ben-Shalom et al.

(10) Patent No.: US 11,679,094 B2
(45) Date of Patent: Jun. 20, 2023

(54) CANNABIDIOL AND CHITOSAN COMPOSITIONS AND METHODS OF USING THE SAME

(71) Applicant: MOR RESEARCH APPLICATIONS LTD., Tel Aviv (IL)

(72) Inventors: Noach Ben-Shalom, Tel Aviv (IL); Dror Robinson, Bat Yam (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 105 days.

(21) Appl. No.: 16/756,575

(22) PCT Filed: Oct. 18, 2018

(86) PCT No.: PCT/IL2018/051119
§ 371 (c)(1),
(2) Date: Apr. 16, 2020

(87) PCT Pub. No.: WO2019/077611
PCT Pub. Date: Apr. 25, 2019

(65) Prior Publication Data
US 2020/0261405 A1    Aug. 20, 2020

Related U.S. Application Data

(60) Provisional application No. 62/573,813, filed on Oct. 18, 2017.

(51) Int. Cl.
A61K 31/352 (2006.01)
A61P 3/06 (2006.01)
A61K 31/05 (2006.01)
A61K 47/10 (2017.01)
A61K 47/24 (2006.01)
A61K 47/36 (2006.01)

(52) U.S. Cl.
CPC ............ *A61K 31/352* (2013.01); *A61K 31/05* (2013.01); *A61K 47/10* (2013.01); *A61K 47/24* (2013.01); *A61K 47/36* (2013.01); *A61P 3/06* (2018.01)

(58) Field of Classification Search
CPC ....... A61K 31/352; A61K 31/05; A61K 47/10
See application file for complete search history.

(56) References Cited

U.S. PATENT DOCUMENTS

| 2010/0158973 A1 | 6/2010 | Weiss |
| 2011/0082195 A1 | 4/2011 | Guy |
| 2013/0011484 A1 | 1/2013 | Bevier |
| 2016/0185679 A1 | 6/2016 | Ghalili et al. |

FOREIGN PATENT DOCUMENTS

| CN | 101977596 A | 2/2011 |
| CN | 103796637 A | 5/2014 |
| WO | 2008068762 A2 | 6/2008 |
| WO | 2016025580 A1 | 2/2016 |

OTHER PUBLICATIONS

PCT International Search Report for International Application No. PCT/IL2018/051119, dated Jan. 9, 2019, 4pp.
PCT Written Opinion for International Application No. PCT/IL2018/051119, dated Jan. 9, 2019, 9pp.
PCT International Preliminary Report on Patentability for International Application No. PCT/IL2018/051119, dated Apr. 21, 2020, 10pp.
Frank D King; G Lawton; A W Oxford Progress in medicinal chemistry. vol. 44. pp. 207-331, Elsevier Science, 2006.

*Primary Examiner* — Kevin E Weddington
(74) *Attorney, Agent, or Firm* — The Roy Gross Law Firm, LLC; Roy Gross

(57) ABSTRACT

The present invention provides a composition based on cannabidiol (CBD) and chitosan for use in reducing blood cholesterol, blood LDL and blood triglycerides levels.

11 Claims, 9 Drawing Sheets

CANNABIDIOL AND CHITOSAN COMPOSITIONS AND METHODS OF USING THE SAME

CROSS REFERENCE

This application is a National Phase of PCT Patent Application No. PCT/IL2018/051119 having International filing date of Oct. 18, 2018, which claims the benefit of priority of U.S. Provisional Patent Application No. 62/573,813 filed on Oct. 18, 2017. The contents of both applications are incorporated herein by reference in their entirety.

FIELD OF INVENTION

This invention is directed to; inter alia, a composition comprising cannabidiol (CBD) and chitosan for improving dyslipidemia and other signs and symptoms of metabolic syndrome.

BACKGROUND OF THE INVENTION

Cannabidiol (CBD), a major non-psychotropic constituent of *Cannabis*, has anti-convulsive, anti-anxiety, anti-psychotic, anti-nausea and anti-rheumatoid arthritic properties. CBD does not bind to the known cannabinoid receptors and its mechanism of action is yet unknown.

CBD was first isolated from Mexican marijuana by Roger Adams and from Indian charas by Alexander Todd, both in 1940. The crystal structure of CBD was determined by Jones et al. (1977). Two independent forms of CBD were noted, which differ mainly in the conformation of the pentyl side chain. The aromatic ring and the terpene ring are almost perpendicular to each other. The two conformers are linked by hydrogen bonding of the hydroxyl moieties.

The chemical nomenclature of CBD differs from that of Tetrahydrocannabinol (THC). While the latter has a pyran ring, which determines its numbering, CBD has no heterocyclic ring and its numbering stems from that of the terpene ring. This, somewhat unfortunate technicality, leads to the same carbon atom being numbered differently in CBD and THC.

The chemistry of CBD has been well explored over the last 50 years. In view of the various, potentially therapeutic, effects caused by CBD, it seems plausible that novel synthetic approaches will still be developed in the future to lead to new types of derivatives.

Chitosan is a naturally occurring positively charged polysaccharide, generally produced by deacetylation of chitin, a naturally occurring biopolymer, found in the cytoskeleton and hard shells of marine organisms such as crustaceans (e.g., shrimps and crabs), and fungi.

Chitosan is biocompatible, non-toxic, and non-immunogenic, allowing its use in the medical, pharmaceutical, and cosmetic fields. The soluble form of chitosan contains positively charged amino groups that can form ionic bonds with anionic compounds, including proteins and fatty acids. Additionally, chitosan may form hydrophobic bonds.

In order to use chitosan in aqueous solution, dissolution of the crystalline structure must take place. In hydrated crystalline chitosan, water molecules form columns between chitosan sheets and contribute to stabilizing the structure by making water-bridges between polymer chains. The hydrogen bonds are broken during the dissolution process of the chitosan using weak organic acids like acetic acid.

Cholesterol is an organic lipid sterol molecule biosynthesized by all animal cells. Cholesterol is an essential structural component of all animal cell membranes; maintaining both membrane structural integrity and fluidity.

Cholesterol serves as a precursor for the biosynthesis of steroid hormones, bile acid, and vitamin D. Cholesterol is carried through the vascular system in structures called lipoproteins. Two kinds of lipoproteins carry cholesterol: low-density lipoproteins (LDL) and high-density lipoproteins (HDL). A high LDL level leads to a buildup of cholesterol in the arteries. HDL carries cholesterol from the body to the liver. In turn the liver removes cholesterol.

High blood cholesterol is a condition which usually has no signs or symptoms. Nonetheless, high blood cholesterol exerts the risk of a coronary heart disease. The higher the level of LDL cholesterol, the greater the chance is of getting a heart disease.

SUMMARY OF THE INVENTION

Figure 1:
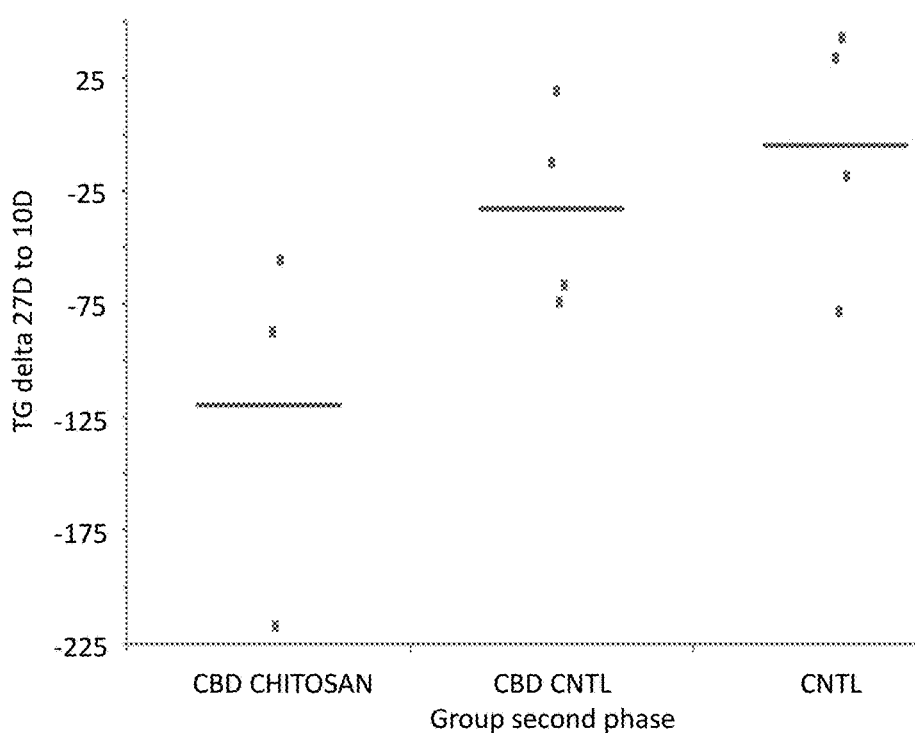
FIG. 1 is a graph showing the effect of cannabidiol (CBD) and chitosan on the concentration of triglycerides in the blood of Guinea pig.

According to one aspect, there is provided a composition comprising: (a) cannabidiol (CBD) and (b) chitosan.

In some embodiments, the composition further comprises an anionic surfactant, a non-ionic surfactant, or a combination thereof.

In some embodiments, the composition further comprises lecithin, a fatty alcohol, or a combination thereof.

In some embodiments, the composition is in the form of a composite particle.

In some embodiments, the composite particle comprises an anionic surfactant, a non-ionic surfactant, or a combination thereof chemically bound to both the chitosan and the CBD.

In some embodiments, the composition comprises: 50 to 600 mg CBD.

In some embodiments, the weight ratio between: (a) the anionic surfactant, the non-ionic surfactant, or a combination thereof; and (b) chitosan; and (c) CBD is from 90:30:1 to 6:2:1 or from 2:1:0.1 to 0.5:1:0.1.

In some embodiments, the composition further comprises Tetrahydrocannabinol (THC).

In some embodiments, the composition further comprises THC in a CBD/THC w/w ratio of 40:1 to 2:1.

In some embodiments, the composition further comprises: CBC, CBG, CBN or any combination thereof.

In some embodiments, the composition is an oral composition, a systemic composition, a topical composition, a rectal composition, a transmucosal composition, a transnasal composition, an intestinal composition or a parenteral composition.

According to another aspect, there is provided a method for decreasing the blood concentration of: cholesterol, LDL, Triglycerides, or any combinations thereof, in a subject in need thereof, comprising administering to the subject the composition disclosed herein, thereby decreasing the blood concentration of: cholesterol, LDL, Triglycerides, or any combinations thereof, in the subject in need thereof.

In some embodiments, the subject is afflicted with hypercholesterolemia. In some embodiments, the subject is afflicted by dyslipidemia. In some embodiments, the subject is afflicted with atherosclerosis.

In some embodiments, the subject is afflicted with a disease or disorder selected from the group consisting of: diabetes mellitus type 2, obesity, alcoholism, monoclonal gammopathy, a kidney disease, nephrotic syndrome, hypothyroidism, Cushing's syndrome, anorexia nervosa, or any combination thereof.

In some embodiments, the subject is treated with a medication selected from the group consisting of: a thiazide diuretic, ciclosporin, a glucocorticoid, a beta blocker, retinoic acid, an antipsychotic, a blood pressure medication, an anticonvulsant, an immunosuppressive, a human immunodeficiency virus therapy, an interferon, or any combination thereof.

In some embodiments, the method further comprises a step of administering an additional cholesterol lowering drug.

In some embodiments, the additional cholesterol lowering drug is selected from the group consisting of: a statin, a bile acid sequestrant, nicotinic acid, fibrates, ezetimibe, or any combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides, in some embodiments, a composition comprising cannabidiol (CBD) and chitosan. In another embodiment, the invention provides a composition comprising: CBD, chitosan and an anionic surfactant, a non-ionic surfactant, or a combination thereof. In another embodiment, the invention provides that an anionic surfactant, a non-ionic surfactant, or a combination thereof are a pharmaceutically acceptable anionic surfactant, a pharmaceutically acceptable non-ionic surfactant, or a pharmaceutically acceptable combination thereof. In another embodiment, the composition can be associated with a cholesterol or triglyceride lowering drug to achieve a combined effect of dyslipidemia correction and or treatment.

In one embodiment, the invention provides a method for treating dyslipidemia in a subject, comprising the steps of: measuring cholesterol blood concentration and/or triglyceride blood concentration in the subject, wherein an elevated or a pathological concentration of cholesterol blood concentration and/or triglyceride blood concentration in the subject further requires the step of: administering a composition, a mixture, and/or particle as described herein. In one embodiment, the invention provides a method for treating dyslipidemia in a subject suffering from an elevated or a pathological concentration of cholesterol and/or triglyceride in the subject's blood, comprising the steps of administering a composition, a mixture, and/or particle as described herein.

In one embodiment, CBD/chitosan w/w ratio of 1:5 to 1:80. In another embodiment, CBD/chitosan w/w ratio of 1:10 to 1:50. In another embodiment, CBD/chitosan w/w ratio of 1:20 to 1:50. In another embodiment, CBD/chitosan w/w ratio of 1:30 to 1:70. In another embodiment, CBD/chitosan w/w ratio of 1:10 to 1:50. In another embodiment, CBD/chitosan w/w ratio of 1:50 to 1:70. In another embodiment, CBD/chitosan w/w ratio of 1:10 to 1:50.

In one embodiment, chitosan comprises a cationic polymer. In one embodiment, chitosan is substituted with a cationic polymer. In one embodiment, chitosan is substituted with a polyamine. In some embodiments, the polyamine comprises polylysine and/or polyacrylamide, or other positively charged polymers. In other embodiments, chitosan is chemically modified by adding other groups such as but not limited to: methylation and acetylation.

In one embodiment, a composition as described herein comprises 50 to 1000 mg cannabidiol (CBD). In one embodiment, a composition as described herein comprises 100 to 1000 mg CBD. In one embodiment, a composition as described herein comprises 100 to 800 mg CBD. In one embodiment, a composition as described herein comprises 200 to 500 mg CBD. In one embodiment, a composition as described herein comprises 200 to 400 mg CBD. In one embodiment, a composition as described herein comprises 50 to 200 mg CBD. In one embodiment, a composition as described herein comprises 250 to 350 mg CBD.

In one embodiment, the term "CBD" includes a functional derivative of CBD. In one embodiment, a functional derivative of CBD a CBD derivative possessing similar, equivalent, or increased CBD efficacy as known in the art. In one embodiment, the phrase "CBD or any functional derivative thereof", according to some embodiments, refers to compounds and/or compositions that are substantially and/or essentially devoid of THC. In one embodiment, a composition as described herein is substantially and/or essentially devoid of THC. In one embodiment, the phrase "CBD or any functional derivative thereof" or composition of the invention, according to some embodiments, refers to compounds and/or compositions wherein the *Cannabis* derived substances include at least 80% CBD or any functional derivative thereof. In one embodiment, the phrase "CBD or any functional derivative thereof" or composition of the invention, according to some embodiments, refers to compounds and/or compositions wherein the *Cannabis* derived substances include at least 85% CBD or any functional derivative thereof. In one embodiment, the phrase "CBD or any functional derivative thereof" or composition of the invention, according to some embodiments, refers to compounds and/or compositions wherein the *Cannabis* derived substances include at least 90% CBD or any functional derivative thereof. In one embodiment, the phrase "CBD or any functional derivative thereof" or composition of the invention, according to some embodiments, refers to compounds and/or compositions wherein the *Cannabis* derived substances include at least 92% CBD or any functional derivative thereof. In one embodiment, the phrase "CBD or any functional derivative thereof" or composition of the invention, according to some embodiments, refers to compounds and/or compositions wherein the *Cannabis* derived substances include at least 95% CBD or any functional derivative thereof. In one embodiment, the phrase "CBD or any functional derivative thereof" or composition of the invention, according to some embodiments, refers to compounds and/or compositions wherein the *Cannabis* derived substances include at least 97% CBD or any functional derivative thereof.

In one embodiment, CBD might contain up to 5% THC or other cannabinoids to produce an entourage effect. In one embodiment, CBD might contain terpenes to facilitate and/or increase its ameliorative metabolic effect. In another embodiment, the composition is combined with a statin. In another embodiment, the methods of the invention include combining the composition of the invention with a statin: (a) within a single dose or a composition; or (b) in separate doses and/or compositions. In another embodiment, methods and compositions combined with a statin such as described herein enhance the efficacy of the given dose of a statin. In another embodiment, methods and compositions combined with a statin such as described herein allow dose reduction of the statin drug without compromising the treatment's efficacy.

In one embodiment, substantially and/or essentially devoid of THC is less than 10% by weight or weight/weight THC. In one embodiment, substantially and/or essentially devoid of THC is less than 7% by weight or weight/weight THC. In one embodiment, substantially and/or essentially devoid of THC is less than 5% by weight or weight/weight THC. In one embodiment, substantially and/or essentially devoid of THC is less than 3% by weight or weight/weight THC. In one embodiment, substantially and/or essentially devoid of THC is less than 1% by weight or weight/weight THC. In one embodiment, substantially and/or essentially devoid of THC is less than 0.5% by weight or weight/weight THC. In one embodiment, substantially and/or essentially devoid of THC is less than 0.3% by weight or weight/weight THC. In one embodiment, substantially and/or essentially devoid of THC is less than 0.1% by weight or weight/weight THC. In one embodiment, a composition as described herein and/or particle comprises THC. In one embodiment, a composition as described herein and/or particle comprises THC in an amount of 0.005% to 1% w/w of the total particle's weight or composition's weight. In one embodiment, a composition as described herein and/or particle comprises THC in an amount of 0.01% to 1% w/w of the total particle's weight or composition's weight. In one embodiment, the composition or particle as described herein comprises THC in a CBD/THC w/w ratio of 40:1 to 2:1. In one embodiment, the composition or particle as described herein comprises THC in a CBD/THC w/w ratio of 20:1 to 8:1. In one embodiment, the composition or particle as described herein comprises CBC, CBG, CBN or any combination thereof.

In one embodiment, a composition as described comprises or has w/w ratio of CBD/CBC, CBG, CBN or any combination thereof of 50:1 to 5:1. In one embodiment, a composition as described comprises or has w/w ratio of a/b of 50:1 to 5:1. In one embodiment, a composition as described comprises or has w/w ratio of a/b of 40:1 to 8:1. In one embodiment, a composition as described comprises or has w/w ratio of a/b of 30:1 to 10:1. In one embodiment, a composition as described comprises or has w/w ratio of a/b of 25:1 to 15:1. In one embodiment, "a" is CBD. In one embodiment, "b" is CBC, CBG, CBN or any combination thereof. In one embodiment, "b" comprises at least two compounds selected from CBC, CBG, and CBN. In one embodiment, "b" comprises at least two compounds selected from CBD, CBC, CBG, and CBN. In one embodiment, "b" is the entire weight of the composition.

In one embodiment, a composition as described herein comprises Tetrahydrocannabinol (THC). In one embodiment, a composition as described herein comprises 0.1 to 120 mg THC. In one embodiment, a composition as described herein comprises 0.5 to 90 mg THC. In one embodiment, a composition as described herein comprises 1 to 80 mg THC. In one embodiment, a composition as described herein comprises 20 to 70 mg THC. In one embodiment, a composition as described herein comprises 1 to 20 mg THC. In one embodiment, a composition as described herein comprises 40 to 90 mg THC.

In one embodiment, the *Cannabis* derived substances used in the composition and methods as described herein include cannabidiol, or a functional variant thereof, free or substantially free of THC. In the methods described herein, purified or substantially purified (greater than 80% w/w, 85% w/w, 90%, w/w 95% w/w or 97% w/w) cannabidiol, or a functional variant thereof, is administered to a subject suffering from a disease or a condition as described herein.

In some embodiments, a CBD-derivative is a metabolite of CBD such as but not limited to: (−)-7-hydroxy-CBD and (−)-CBD-7-oic acid and their dimethylheptyl (DMH) homologs, as well as of the corresponding compounds in the enantiomeric (+)-CBD series. A CBD derivative is characterized, in some embodiments, by a structure wherein at least one of the hydroxyl substituent groups is converted to a stable form thereof. In one embodiment, a CBD derivative is cannabinol comprising a quinone ring. In one embodiment, a CBD derivative is an endocannabinoid derivative. In some embodiments, a CBD derivative is described in Frank D King; G Lawton; A W Oxford Progress in medicinal chemistry. Vol. 44. Pages 207-331, Elsevier Science, 2006 ISBN: 0080462103 9780080462103 which is hereby incorporated by reference in its entirety.

According to some embodiments, the anionic surfactant is selected from the group consisting of a phospholipid, a bile salt, sodium lauryl ether sulfate, a citric acid ester of monoglyceride, sodium, calcium, acid stearoyl lactylate, stearyl citrate, fatty acid, a salt of a fatty acid, diacetyl tartaric acid ester of monoglyceride, or any combinations thereof.

In one embodiment, the phospholipid comprises lecithin. In one embodiment, the non-ionic surfactant is a fatty alcohol.

According to some embodiments, the surfactant is selected from the group consisting of phospholipids; bile salts; sodium lauryl ether sulfate; citric acid esters of monoglycerides; sodium, calcium or acid stearoyl lactylate; stearyl citrate; fatty acids or salts thereof; diacetyl tartaric acid esters of monoglycerides; or combinations thereof. In one embodiment, the non-ionic surfactants include cetyl alcohol or oleyl alcohol. In one embodiment, the anionic surfactant comprises the phospholipids, lecithin (phosphatidylcholine), also known as 1,2-diacyl-sn-glycero-3-phosphocholine, or PtdCho. In one embodiment, the surfactant comprises a mixture of phospholipids. In one embodiment, the surfactant or lecithin comprises: a glycerophospholipid, phosphatidylcholine, phosphatidylethanolamine, phosphatidylinositol, phosphatidic acid, or any mixture thereof. In one embodiment, lecithin is hydrolyzed lecithin.

In one embodiment, a composition or a mixture as described herein is provided within a form of single particle. In one embodiment, a particle comprises CBD and chitosan. In one embodiment, a particle comprises a composition as described herein. In one embodiment, a particle comprises CBD, chitosan and an anionic surfactant, a non-ionic surfactant, or a combination thereof. In one embodiment, a particle is a composite particle. In one embodiment, a particle comprises CBD bound to an anionic or non-ionic surfactant. In one embodiment, a particle as described herein comprises CBD and chitosan bound to an anionic or non-ionic surfactant.

In one embodiment, a particle as described herein comprises CBD and chitosan in sperate compartments. In one embodiment, CBD and chitosan are not in contact within a particle as described herein.

In one embodiment, a particle as described herein comprises cationic polymer chemically bound to an anionic or non-ionic surfactant, wherein CBD and chitosan are bound to the anionic or the non-ionic surfactant. In one embodiment, a particle as described herein is a composite or a composition comprising CBD-chitosan-lecithin particle. According to some embodiments, the particle and/or composition is a dry particle and/or composition having a water content of less than 25% w/w. According to some embodiments, the particle and/or composition is a dry particle and/or composition having a water content of less than 20% w/w. According to some embodiments, the particle and/or composition is a dry particle and/or composition having a water content of less than 10% w/w. According to some embodiments, the particle and/or composition is a dry particle and/or composition having a water content of less than 7% w/w. According to some embodiments, the particle and/or composition is a dry particle and/or composition having a water content of less than 5% w/w. According to some embodiments, the particle and/or composition is a dry particle and/or composition having a water content of less than 3% w/w. According to some embodiments, the particle and/or composition is a dry particle and/or composition having a water content of less than 2% w/w. According to some embodiments, the particle and/or composition is a dry particle and/or composition having a water content of less than 1% w/w.

In some embodiments, the particle and/or composition is in the form of a flowing powder. In some embodiments, the particle and/or composition is in the form of a packed powder. In some embodiments, the particle and/or composition is in the form of a mixture of granular particles.

According to some embodiments, the composite particles, the mixture and/or the composition is/are capable, upon mixing 2.5 grams of the composite particles of the mixture with 1 liter of a sodium cholate solution having a sodium cholate concentration of 0.5% w/w, of removing at least 10% of free sodium cholate from the sodium cholate solution within 30 minutes.

According to some embodiments, the composite particles of the mixture are capable, upon mixing 2.5 grams of the composite particles of the mixture with 1 liter of a sodium cholate solution having a sodium cholate concentration of 0.5% w/w, of removing at least 20% of free sodium cholate from the sodium cholate solution within 30 minutes.

According to some embodiments, the composite particles of the mixture are capable, upon mixing 2.5 grams of the composite particles of the mixture with 1 liter of a sodium cholate solution having a sodium cholate concentration of 0.5% w/w, of removing at least 30% of free sodium cholate from the sodium cholate solution within 30 minutes.

According to some embodiments, the composite particles of the mixture are capable, upon mixing 2.5 grams of the composite particles of the mixture with 1 liter of a sodium cholate solution having a sodium cholate concentration of 0.5% w/w, of removing at least 40% of free sodium cholate from the sodium cholate solution within 30 minutes.

In one embodiment, at least 10%, by mass, of the composite particles have a size between 0.1 microns and 50 microns. In one embodiment, at least 10%, by mass, of the composite particles have a size between 0.2 microns and 20 microns. In one embodiment, at least 10%, by mass, of the composite particles have a size between 0.4 microns and 15 microns.

In one embodiment, at least 30%, by mass, of the composite particles of the mixture have a size between 0.3 microns and 5 microns. In one embodiment, at least 30%, by mass, of the composite particles of the mixture have a size between 0.3 microns and 20 microns. In one embodiment, at least 50%, by mass, of the composite particles of the mixture have a size between 0.3 microns and 20 microns. In one embodiment, at least 50%, by mass, of the composite particles of the mixture have a size between 0.3 microns and 10 microns. In one embodiment, at least 70%, by mass, of the composite particles of the mixture have a size between 0.3 microns and 40 microns. In one embodiment, at least 70%, by mass, of the composite particles of the mixture have a size between 0.3 microns and 20 microns. In one embodiment, at least 70%, by mass, of the composite particles of the mixture have a size between 0.3 microns and 10 microns. In one embodiment, at least 70%, by mass, of the composite particles of the mixture have a size between 0.3 microns and 5 microns.

In one embodiment: i) the composite particles of the mixture are capable, upon mixing 2.5 grams of the composite particles of the mixture with 1 liter of a sodium cholate solution having a sodium cholate concentration of 0.5% w/w, of removing at least 15% of free sodium cholate from the sodium cholate solution within 30 minutes; and ii) at least 30%, by mass, of the composite particles of the mixture have a size between 0.3 microns and 20 microns. According to some embodiments, i) the composite particles of the mixture are capable, upon mixing 2.5 grams of the composite particles of the mixture with 1 liter of a sodium cholate solution having a sodium cholate concentration of 0.5% w/w, of removing at least 35% of free sodium cholate from the sodium cholate solution within 30 minutes; and ii) at least 30%, by mass, of the composite particles of the mixture have a size between 0.3 microns and 20 microns.

According to some embodiments, the composite particles have a lecithin-chitosan mass ratio of between 0.1:3 and 15:1. According to some embodiments, the composite particles have a lecithin-chitosan mass ratio of between 0.1:1 and 6:1. According to some embodiments, the composite particles have a lecithin-chitosan mass ratio of between 0.2:1 and 6:1. According to some embodiments, the composite particles have a lecithin-chitosan mass ratio of between 0.2:1 and 5:1. According to some embodiments, the plurality of composite particles include composite particles having a lecithin-chitosan mass ratio of between 3:1 and 4:1.

According to some embodiments, the composite particles have a lecithin-chitosan-CBD mass ratio of between 0.1:3: 0.02 and 15:1:0.1. According to some embodiments, the composite particles have a lecithin-chitosan-CBD mass ratio of between 0.1:1:0.01 and 6:1:0.2. According to some embodiments, the composite particles have a lecithin-chitosan-CBD mass ratio of between 0.2:1:0.05 and 6:1:0.5. According to some embodiments, the composite particles have a lecithin-chitosan-CBD mass ratio of between 0.2:1: 0.001 and 5:1:0.02. According to some embodiments, the plurality of composite particles include composite particles having a lecithin-chitosan-CBD mass ratio of between 3:1: 0.05 and 4:1:0.1. In some embodiments, the chitosan, CBD and the lecithin of the composite particles are chemically bound by at least one of ionic and hydrophobic interactions.

In one embodiment, chitosan has a degree of deacetylation of between 50% and 95%. In one embodiment, chitosan as described herein has molecular weight between 3800 and 20,000 Daltons. In one embodiment, chitosan as described herein has molecular weight between 100,000 and 3,000,000 Daltons. In one embodiment, chitosan as described herein has molecular weight between 50,000 and 500,000 Daltons. In one embodiment, chitosan as described herein has molecular weight between 1,000,000 and 3,000,000 Daltons. In one embodiment, chitosan comprises alpha-chitosan. In one embodiment, chitosan comprises beta-chitosan. In one embodiment, chitosan is a mixture of alpha-chitosan and beta-chitosan.

In one embodiment, a composition, a particle and/or a mixture such as described herein is useful for lowering blood cholesterol concentration. In one embodiment, a composition, a particle and/or a mixture such as described herein is useful for lowering blood low-density lipoprotein (LDL) concentration. In one embodiment, a composition, a particle and/or a mixture such as described herein is useful for lowering blood triglycerides concentration. In one embodiment, a composition, a particle and/or a mixture such as described herein is useful for sequestering triglycerides, cholesterol, and/or LDL in the blood. In one embodiment, a composition, a particle and/or a mixture such as described herein is useful for treating a subject afflicted with dyslipidemia. In one embodiment, a composition, a particle and/or a mixture such as described herein is useful for reducing relative the of a cardiovascular disease in a subject. In one embodiment, a composition, a particle and/or a mixture such as described herein is useful for treating a subject afflicted with atherosclerosis. In one embodiment, a composition, a particle and/or a mixture such as described herein is useful for lowering the concentration of C-reactive protein (CRP) in the blood of a subject or for lowering the concentration of other inflammatory agents/mediators such as but not limited to: IL-6 and IL-1. In one embodiment, a composition, a particle and/or a mixture such as described herein is useful for raising the concentration of high-density lipoprotein cholesterol (HDL-C) and lowering the concentration of LDL-C in the blood of a subject in need thereof.

In one embodiment, provided herein is a method for the preparation of a composition or a particle as described herein, comprising: a) providing a plurality of chitosan particles; b) mixing the plurality of chitosan particles and CBD into an acid to obtain a first solution; c) preparing a second solution comprising an anionic or non-ionic surfactant; and d) mixing the first and second solutions under acidic conditions to form CBD-chitosan-surfactant composite particles including chitosan and CBD chemically bound to the surfactant. In one embodiment, a method for the preparation of a composition or a particle as described herein may further comprise step e) comprising forming a powder from the chitosan-surfactant and CBD-surfactant composite particles.

In one embodiment, forming a powder comprises spray-drying, lyophilization, or both. In one embodiment, the second solution is an aqueous solution. In one embodiment, the concentration of the chitosan in the mixture of the first solution is between 0.1% w/w to 4.5% w/w. In one embodiment, the concentration of the chitosan in the mixture of the first solution is between 0.15% w/w to 1.5% w/w. In one embodiment, the concentration of the chitosan in the mixture of the first solution is between 0.25% w/w to 1% w/w. In one embodiment, the concentration of CBD in the mixture of the first solution is between 0.001% w/w to 0.5% w/w. In one embodiment, the concentration of CBD in the mixture of the first solution is between 0.005% w/w to 0.1% w/w. In one embodiment, the concentration of CBD in the mixture of the first solution is between 0.001% w/w to 0.1% w/w. In one embodiment, the concentration of lecithin in the second solution is between 0.1% w/w to 15.0% w/w. In one embodiment, the concentration of lecithin in the second solution is between 0.5% w/w to 10.0% w/w. In one embodiment, the concentration of lecithin in the second solution is between 1% w/w to 5.0% w/w.

In one embodiment, mixing is mixing with an acid. In one embodiment, the acid is an organic acid selected from the group consisting of lactic acid and glutamic acid. In one embodiment, a particle as described herein comprises an acid. In one embodiment, a particle as described herein comprises lactic acid, glutamic acid, or a combination thereof.

In one embodiment, the method further comprises the step of adjusting the pH of the combined first and second solutions to a value of 6.5 to 7.5. In one embodiment, the method further comprises the step of adjusting the pH of the combined first and second solutions to a value of 6.7 to 7.3. In one embodiment, the method further comprises the step of adjusting the pH of the combined first and second solutions to a value of 6.8 to 7.2. In one embodiment, the method further comprises the step of adjusting the pH of the combined first and second solutions to a value of 6.9 to 7.1.

In one embodiment, a composition as described herein is formulated to a suitable route of administration, such as: oral, rectal, transmucosal, topical, transnasal, intestinal or parenteral delivery, including intramuscular, intra articular periligamentous, subsynovial periarticular subcutaneous and intramedullary injections as well as intrathecal, direct intraventricular, intravenous, intraperitoneal, intranasal, or intraocular injections.

Oral administration of a composition as described herein, in one embodiment, comprises a unit dosage form comprising tablets, capsules, lozenges, chewable tablets, suspensions, emulsions and the like.

The pharmaceutically-acceptable carriers suitable for the preparation of unit dosage forms of a composition as described herein for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises a dosage form (composition) or dosage forms having different release profile for each of the active compounds described herein. In one embodiment, the oral dosage form of the present invention comprises a dosage form (composition) or dosage forms having the same release profile for each of the active compounds described herein. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.0012% to about 0.933% w/w or w/v of CBD and chitosan, or in another embodiment, from about 0.0033% to about 0.7% w/v or w/w.

In some embodiments, compositions for use in the methods of this invention comprise solutions or emulsions, which in some embodiments are aqueous solutions or emulsions comprising a safe and effective amount of CBD and chitosan of the present invention and optionally, other compounds as described herein, including excipients intended for topical intranasal administration.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention are formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In another embodiment, CBD and chitosan can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition or compositions are delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N Engl. J. Med.* 321:574 (1989). In another embodiment, further polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (*Science* 249:1527-1533 (1990).

In some embodiments, at least one of the active ingredients is in a powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polyglycolic acid, hydrogels, etc., or onto liposomes, microemulsions, ratslles, unilamellar or multilamellar vesicles, erythrocyte ghosts, or spheroplasts. Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is affected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, provided a method for treating a subject according to the usages and methods of the invention, comprising daily administering to the subject a composition as described herein. In one embodiment, provided a method for treating a subject according to the usages and methods of the, comprising weekly administering to the subject a composition as described herein. In one embodiment, provided a method for treating a subject according to the usages and methods of the invention, comprising twice a day administering to the subject a composition as described herein. In one embodiment, provided a method for treating a subject according to the usages and methods of the invention, comprising 1-4 times a day administering to the subject a composition as described herein.

In another embodiment, the subject is a mammal. In another embodiment, the subject is a lab animal. In another embodiment, the subject is a pet. In another embodiment, the subject is a rodent. In another embodiment, the subject is a farm animal. In another embodiment, the subject is a human subject.

Any concentration ranges, percentage range, dose/dosage or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as weight, is to be understood to include any integer within the recited range, unless otherwise indicated.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a", "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Example 1

Anti Dyslipidemic Effects of Chitosan-Lecithin/Cbd Formulations in the Guinea Pig Induced Dyslipidemia Model The objective of this research was to examine the cholesterol blood levels of guinea pigs, fed ad libitum a high-level fat diet rich in lauric and myristic acids alone or in combination with various formulations.

The blood cholesterol and triglycerides were examined in male guinea pigs, following an oral administration of the various formulations in correlation to the Controlled group.

Measurement of cholesterol, and Triglyceride levels in the serum were performed following a 7-10 day of exposure to the different diets.

Animals

The mean body weights were 370 g at study initiation. The minimum and maximum weights of the group did not exceed±20% of group mean body weight.

During acclimation animals were fed ad libitum "free-feeding" a commercial guinea pig diet (Harlan Teklad Guinea Pig Diet cat #: 2040S).

Animals had free access to drinking water obtained from the municipality supply.

TABLE 1

| Group Designation Parameters | | | | | |
|---|---|---|---|---|---|
| Gp. | n | Treatment | (mg/g) diet) | Dose Level mg/kg | Route |
| CNTL fattening | 20 | Fattening diet | 0 | NA | oral |
| Chitosan Diet | 4 | Fattening diet and Lechit4: 1 L | 40 | 1600 mg | |
| CBD | 4 | Fattening diet and CBD | 2.3 | 92 mg | |
| CBD Chitosan | 3 | Fattening diet and CBD Lechit4: 1 L | 40/2.3 | 1600 mg Lecit4: 1 L and 92 mg CBD | |

Study Initiation Definition

"Day 0" was initiation of the Study period, animals received regular guinea pig diet. Day 3 the animals were subjected to blood withdrawal and subsequently the first day of supplying the fattening diet. On day 11 chitosan diet was administered to the relevant group. On day 24 CBD diet and CBD chitosan diet were administered until day 27.

Test Item Administration

Ready to use putty for the chitosan diet, provided ad libitum;
Ready to use putty for the chitosan-CBD diet, provided ad libitum;
Ready to use pellets for the CBD diet, provided ad libitum Body Weight Measurement Determination of individual body weights of animals was conducted once weekly during the entire study.
Days 3-4;
Days 11-14 for the chitosan and fattening diet group;

The procedure was performed for 24-72 hours. Determination of food consumption (gr/animal calculated value) is based on provided diet placed in hoppers and unused diet including noticeable scatter. This measurement is not exact due to the animals' tendency to throw food from cage to cage and all over the floor.

Blood Collection

Day 3 all animals; Day 11 all animals; Day 24 all animals; Day 27 CBD, CNTL-fattening and CBD-chitosan group.

The blood collection tubes (BD 367955) were specialized for serum separation, containing a clot activator and a gel which separates the cell content (pellet) from the serum (supernatant) after centrifugation. Blood samples of ~0.5 mL/animal were collected into the pre-marked tubes (study code, animal number and date). At all times blood was collected under anesthesia: Ketamine 20-40 mg/kg & Diazepam 1-2 mg/kg IM. Blood collection of all animals was performed via the periorbital eye venous plexus puncture.

Serum Preparation

Blood samples were left at room temperature for at least 45 minutes, and subsequently centrifuged (4000 RCF, 1790 g, 10 min/RT) for serum separation and left in the specialized tubes with the gel partitioning the separated serum and cell content. The samples were transferred as such to AML.

Blood Lipid Profile Determination

Following serum separation, the samples were kept at 2-8° C. until transferred to AML, for blood lipid profile analysis (cholesterol, LDL, HDL and Triglyceride levels). Sample transfer was via wet ice packed in Styrofoam boxes and transferred within 1-2 hours from blood separation.

Materials and Methods

Formulations

TABLE 2

| Control: | |
|---|---|
| Name: | DietD110239 |
| Manufacturer: | TEKLAD, INC. |
| Chemical Name/Formulation: | See appendix I |
| Storage conditions: | Room Temperature |
| Expiry Date: | 2018 |
| Name to be used in the report: | Controlled diet |
| Date of receipt at test facility: | 28 Jun. 2017 |
| Purity to be stated in the report: | NA |
| Physical appearance (Test item): | Soft pellets |
| Name (formulated diet): | Fattening Diet |
| Physical appearance (formulated diet): | Pelleted diet |

TABLE 3

| Test item 1: | |
|---|---|
| Name: | Lechit4: 1 L (0.3% concentration) |
| Manufacturer: | Sponsor |
| Chemical Name/Formulation: | NA |
| Storage conditions: | Room Temperature |
| Expiry Date: | NA |

TABLE 3-continued

Test item 1:

| | |
|---|---|
| Name to be used in the report: | Lechit4: 1 L |
| Date of receipt at test facility: | 3 Aug. 2017 |
| Purity to be stated in the report: | NA |
| Physical appearance (Test item): | Fine off-white powder |
| Name (formulated diet): | Chitosan diet |
| Physical appearance (formulated diet): | Putty semi-dry |

TABLE 4

Test item 2:

| | |
|---|---|
| Name: | CBD |
| Manufacturer: | Scientific Health Solutions |
| Chemical Name/Formulation: | Cannabidiol |
| Storage conditions: | RT |
| Expiry Date: | August 2019 |
| Name to be used in the report: | CBD |
| Date of receipt at test facility: | 27 Aug. 2017 |
| Purity to be stated in the report: | No less than 99% |
| Physical appearance (Test item): | Blue gel |
| Name (formulated diet): | CBD |
| Physical appearance (formulated diet): | Pellets |

TABLE 5

Test item 2:

| | |
|---|---|
| Name: | CBD Lecit4: 1 L |
| Manufacturer: | Scientific Health Solutions |
| Chemical Name/Formulation: | Cannabidiol and Chitosan-Lecithin particle |
| Storage conditions: | RT |
| Expiry Date: | NA |
| Name to be used in the report: | CBD-Chitosan |
| Date of receipt at test facility: | 27 Aug. 2017 |
| Purity to be stated in the report: | Not less than 99% |
| Physical appearance (Test item): | Blue putty |
| Name (formulated diet): | CBD-Chitosan |
| Physical appearance (formulated diet): | Bluish putty |

Vehicle for CBD: CBD:Olive Oil 2,800 mg/10 ml vol
Formulation of the Test Items

Pelleted diet: TEKLAD prepared a custom diet designed to induce elevation of cholesterol levels and induction of dyslipidemia in Guinea pigs. All diets were provided to the test facility as a ready to use pelleted diets, sterilized and vacuum packed.

Chitosan Diet

Dose level 80 grams of Lechit4:1 L/2 kg DietD110239.

Preparation of chitosan diet: 2 kg of DietD110239 were grounded into powder, 80 grams of Lecit4:1 L were added, 330 ml of tap water were added, the obtained paste was thoroughly mixed.

CBD Diet

Dose level 1.4 grams CBD/600 g DietD110239.

Preparation of CBD diet: 600 g DietD110239 were grounded into powder. 1.4 grams of CBD in 10 ml oil were added. the obtained paste was thoroughly mixed.

Combination of CBD and Chitosan Diet

Dose level 1.4 grams CBD/600 g chitosan diet.

Preparation of CBD and chitosan diet: 600 g chitosan diet were grounded into powder. 1.4 grams of CBD in 10 ml oil were added, 30 ml of tap water were added, the obtained paste was thoroughly mixed.

Results

Group chitosan fattening diet consists of four animals, namely animals (1-4), Group fattening diet consists of 16 animals from whom 4 had the food consumption (numbers 5-8), Group CBD Chitosan consists of 3 animals (1-3) treated sequentially following treatment with Chitosan. Group CBD consists of four animals (8-12).

All groups showed a positive BW gain (see table 6).

TABLE 6

| | | | | |
|---|---|---|---|---|
| CHITOSAN | 4 | 102.0 | 13.96 | 21.5 |
| CNTL | 8 | 92.3 | 9.87 | 30.3 |
| Pooled | 12 | | | 27.9 |

* Standard error of the mean.

| DELTA WEIGHT (grams) | First Phase Group |
|---|---|
| 78.00 | CHITOSAN |
| 103.00 | CHITOSAN |
| 130.00 | CHITOSAN |
| 97.00 | CHITOSAN |
| 57.00 | CNTL |
| 95.00 | CNTL |
| 128.00 | CNTL |
| 91.00 | CNTL |
| 60.00 | CNTL |
| 87.00 | CNTL |
| 77.00 | CNTL |
| 143.00 | CNTL |

Table 6 provides the results of animal weight gain from study initiation following the first phase treatment, per group.

TABLE 7

| DELTA WEIGHT to by Second phase Group | N | Mean | Mean SE* | SD |
|---|---|---|---|---|
| CBD | 4 | 132.0 | 15.43 | 20.0 |
| CHITOSAN + CBD | 3 | 81.3 | 17.82 | 54.0 |
| CNTL | 4 | 134.8 | 15.43 | 13.8 |
| Pooled | 11 | | | 30.9 |

*Standard error of the mean based on the pooled sample variance.

| DELTA WEIGHT | Second phase Group |
|---|---|
| 122.00 | CHITOSAN + CBD |
| 102.00 | CHITOSAN + CBD |
| 20.00 | CHITOSAN + CBD |
| 123.00 | CNTL |
| 135.00 | CNTL |
| 127.00 | CNTL |
| 154.00 | CNTL |
| 130.00 | CBD |
| 108.00 | CBD |
| 133.00 | CBD |
| 157.00 | CBD |

Table 7 provides the results of animal weight at study initiation and following second phase treatment.

The change in weight in the chitosan and CBD group (see table 8) was less than in the other groups, though the difference is not statistically significant when tested by ANOVA change in weight during treatment versus each group.

Table 8

| Weight Change at 30-Aug-2017 versus BL by combined effect on weight | N | Mean | Mean SE* | SD |
|---|---|---|---|---|
| Chitosan and CBD | 3 | 185.0 | 22.09 | 30.4 |
| CNTL | 8 | 225.6 | 13.53 | 40.2 |
| Pooled | 11 | | | 38.3 |

N = 11

ANOVA

| Source | SS | DF | MS | F | p-value |
|---|---|---|---|---|---|
| combined effect on weight | 3600.9 | 1 | 3600.9 | 2.46 | 0.1512 |
| Error | 13171.9 | 9 | 1463.5 | | |
| Total | 16772.7 | 10 | 1677.3 | | |

Multiple Comparisons

Student's individual comparisons

| Contrast | Mean difference | Individual 95% CI | SE | 0 | p-value |
|---|---|---|---|---|---|
| CNTL – CHIT CBD | 53.4 | -0.9 to 107.8 | 23.57 |  | 0.0532[1] |
| CBD – CHIT CBT | 50.7 | -3.7 to 105.0 | 23.57 |  | 0.0638[1] |
| CNTL – CBD | 2.8 | -47.6 to 53.1 | 21.82 |  | 0.9028[1] |

H0: θ=0
The difference between the means of the populations is equal to 0.
H1: θ≠0
The difference between the means of the populations is not equal to 0.
[1] Do not reject the null hypothesis at the 5% significance level.

N | 15

| Change in Weight by group | N | Mean | Mean SE* | SD |
|---|---|---|---|---|
| CBD | 4 | 58.8 | 11.82 | 16.5 |
| CHIT | 4 | 24.3 | 11.82 | 38.4 |
| CHIT CBD | 3 | 48.3 | 13.65 | 12.6 |
| CNTL | 4 | 64.8 | 11.82 | 14.0 |
| Pooled | 15 | | | 23.6 |

* Standard error of the mean based on the pooled sample variance.

Multiple Comparisons

Student's individual comparisons

| Contrast | Mean difference | Individual 95% CI | SE | 0 | p-value |
|---|---|---|---|---|---|
| CNTL – CHIT | 40.5 | 3.7 to 77.3 | 16.72 | | 0.0339[1] |
| CBD – CHIT | 34.5 | -2.3 to 71.3 | 16.72 | | 0.0635[2] |
| CHIT CBD – CHIT | 24.1 | -15.7 to 63.8 | 18.06 | | 0.2093[2] |
| CNTL – CHIT CBD | 16.4 | -23.3 to 56.2 | 18.06 | | 0.3828[2] |
| CBD – CHIT CBD | 10.4 | -29.3 to 50.2 | 18.06 | | 0.5757[2] |
| CNTL – CBD | 6.0 | -30.8 to 42.8 | 16.72 | | 0.7265[2] |

H0: Θ=0
The difference between the means of the populations is equal to 0.
H1: Θ≠0
The difference between the means of the populations in not equal to 0.
1 Reject the hypothesis in favor of the alternative hypothesis at the 5% significance level.

Table 7 provides the results of weight gain of the Chitosan and CBD treatment group. From baseline weight gain was about 10 percent less than the control group (the difference was not significant).

Food Consumption

First FC Days 3-4: The per cage food consumption was approximately the same in all the cages, ranging from 120-150 grams.

Second FC Days 13-14: Chitosan cage 145-180 grams per day, CNTL cage 100-140 grams per day Third FC Days 24-27: Chitosan and CBD group 180-200 grams per cage per day (3 animals). CBD group 150-200 grams per day per cage. CNTL 150-170 grams per day per cage Blood Chemistry The difference between the group treated with a chitosan diet with CBD added at the second phase (CBD CHITOSAN) and the control (CNTL) group was significant (see FIG. 1 and Table 9).

TABLE 9

| TG delta 27D to 10D by group second phase | N | Mean | Mean SE* | SD |
|---|---|---|---|---|
| CBD CHITOSAN | 3 | −119.7 | 35.39 | 85.8 |
| CBD CNTL | 4 | −33.0 | 30.65 | 44.8 |
| CNTL | 4 | −4.8 | 30.65 | 55.7 |
| Pooled | 11 | | | 61.3 |

*Standard error of the mean based on the pooled sample variance.
Student's t individual comparisons

| Contrast | Mean difference | Individual 95% CI | SE | θ | | p-value |
|---|---|---|---|---|---|---|
| CNTL - CBD CHITOSAN | 114.9 | 6.9 to 222.9 | 46.82 | 0 | 215.9 | 0.0397 [1] |
| CBD CNTL - CBD CHITOSAN | 86.7 | −21.3 to 194.6 | 46.82 | 21.30432712 | 194.6 | 0.1013 [2] |
| CNTL - CBD CNTL | 28.3 | −71.7 to 128.2 | 43.35 | 71.71171624 | 128.2 | 0.5329 [2] |

H0: θ = 0
The difference between the means of the populations is equal to 0. H1: θ ≠ 0 The difference between the means of the populations is not equal to 0.
[1] Reject the null hypothesis in favor of the alternative hypothesis at the 5% significance level.
[2] Do not reject the null hypothesis at the 5% significance level.

Figure 2:
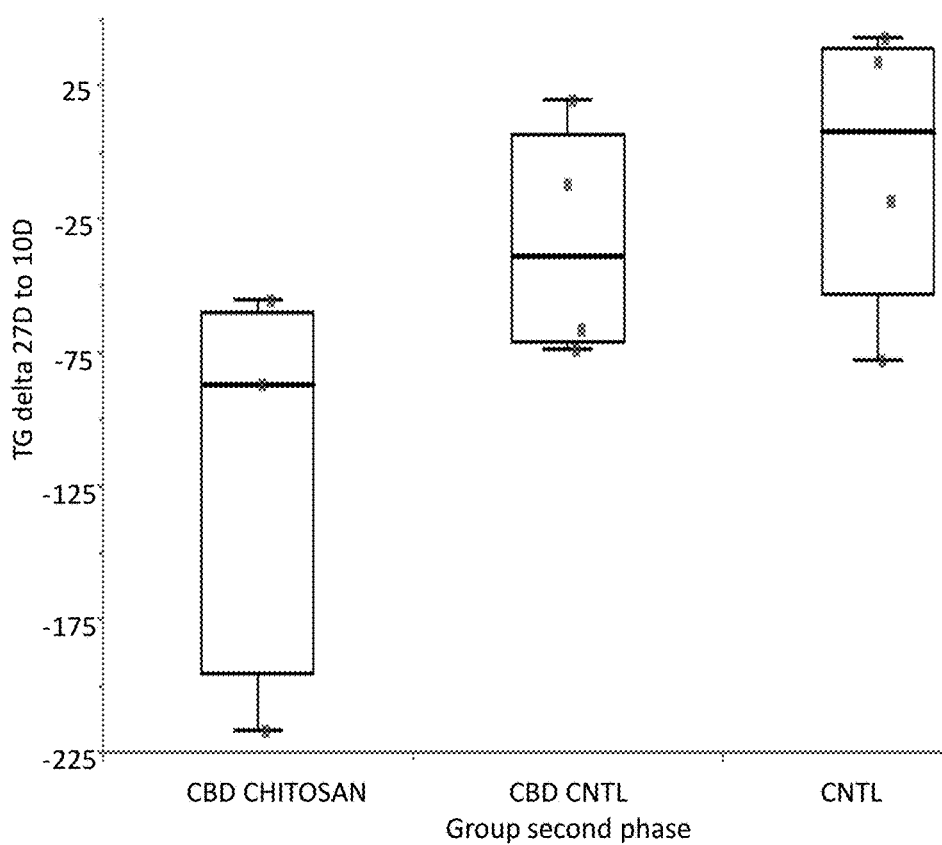
FIG. 2 is a graph showing the effect of CBD and chitosan on the concentration of triglycerides (TG) in the blood of guinea pig.
Figure 3:
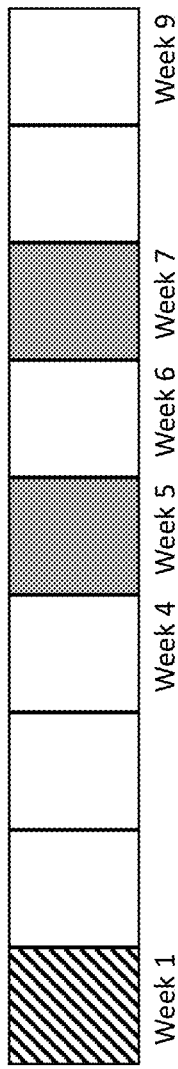
FIG. 3 is a schematic illustration of a study time line performed in rats to examine the effects of Chitosan-Lecithin-CBD (CLC)-enriched diet in rats. The study was divided into several phases as follows: Acclimation period (7 days—rat maintenance diet (RMD); Study period 1 (21 days of high fat and high sucrose (HFHS) diet to all animals); Study period 2 (7 days of CLC diet); Study period 3 (7 days of HFHS diet); Study period 4 (7 days of CLC diet); and Study period 5 (14 days of HFHS diet). Diagonal stripes filling—RMD diet; White box—HFHS diet ($1^{st}$ week to $3^{rd}$ week are 'Interval one'; $4^{th}$ week is 'Interval two', $5^{th}$ week to $6^{th}$ week are 'Interval three'); Grey box—HFHS diet with CLC (15 mg per day expected daily dose). Arrows denote times of blood sampling.
Figure 4:
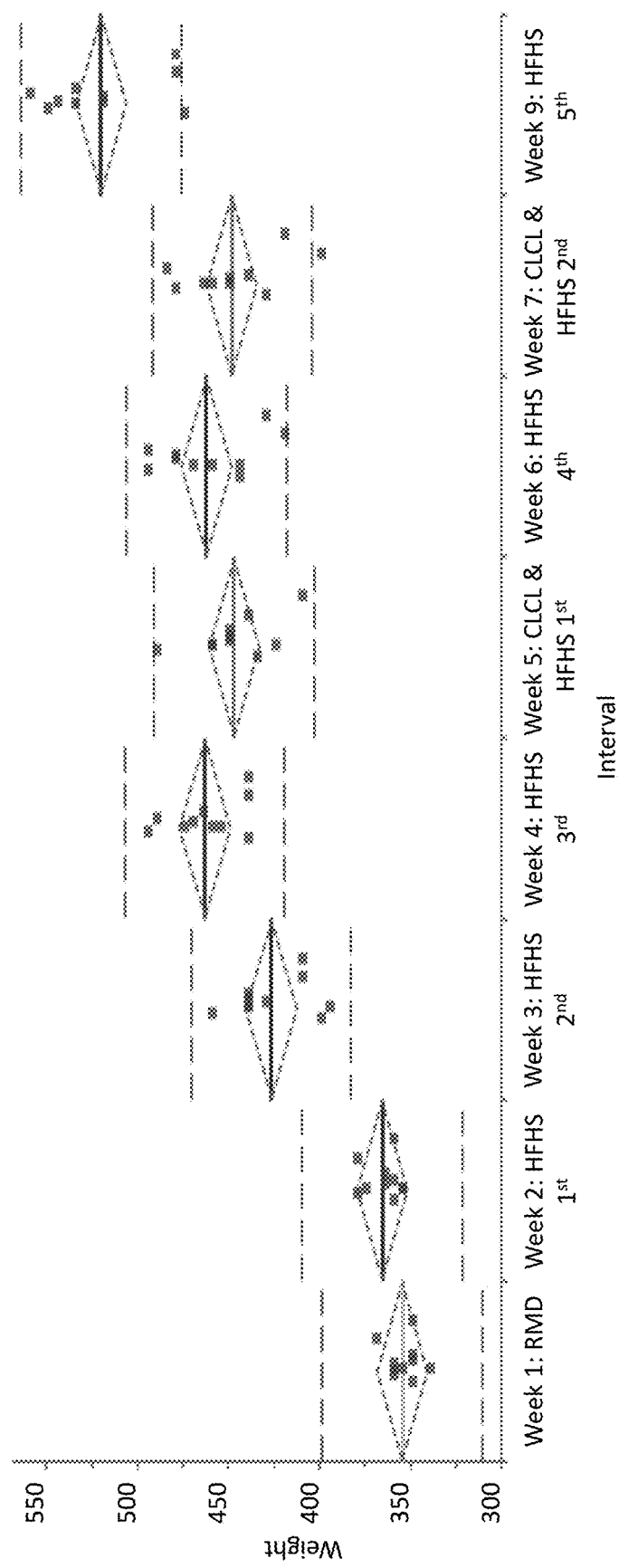
FIG. 4 is a graph showing the weights of rats fed on CLC-enriched diet.
Figure 5:
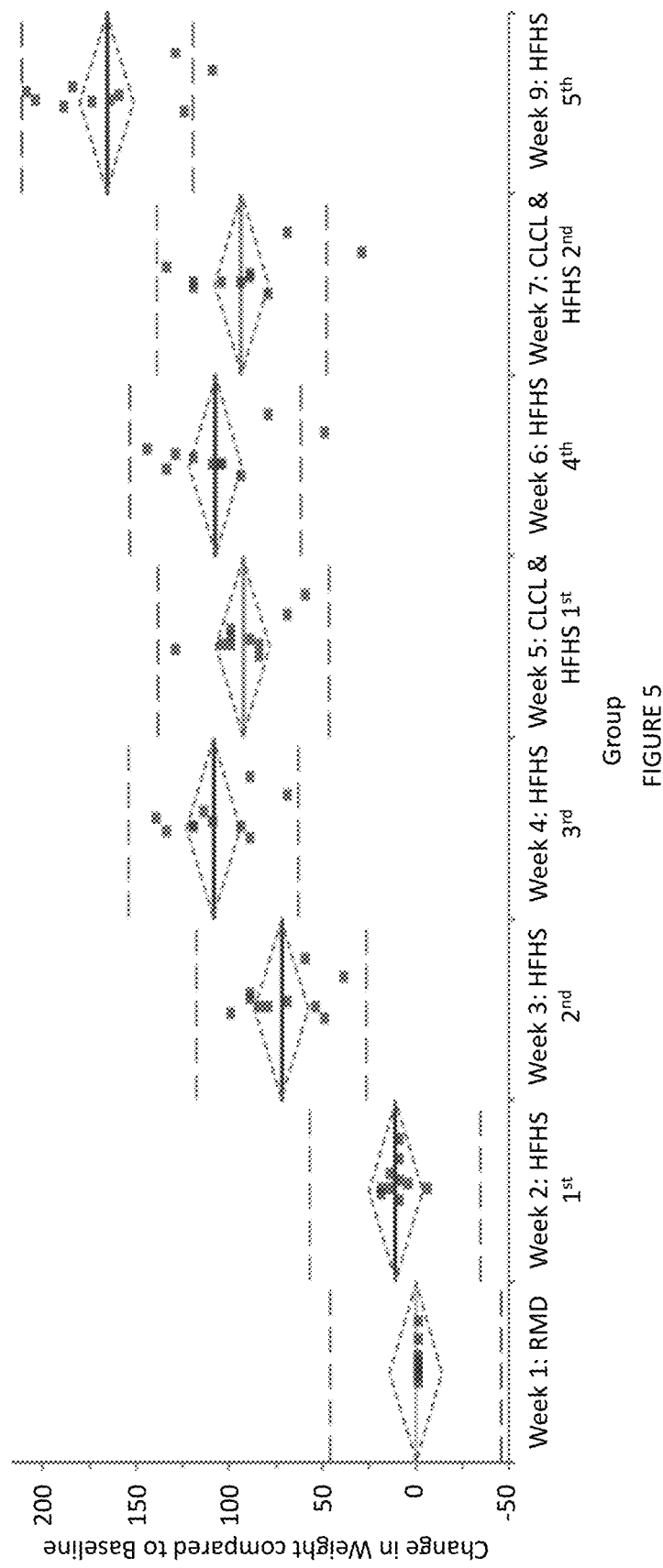
FIG. 5 is a graph showing the weights of rats fed on CLC-enriched diet compared to their basal weights.
Figure 6:
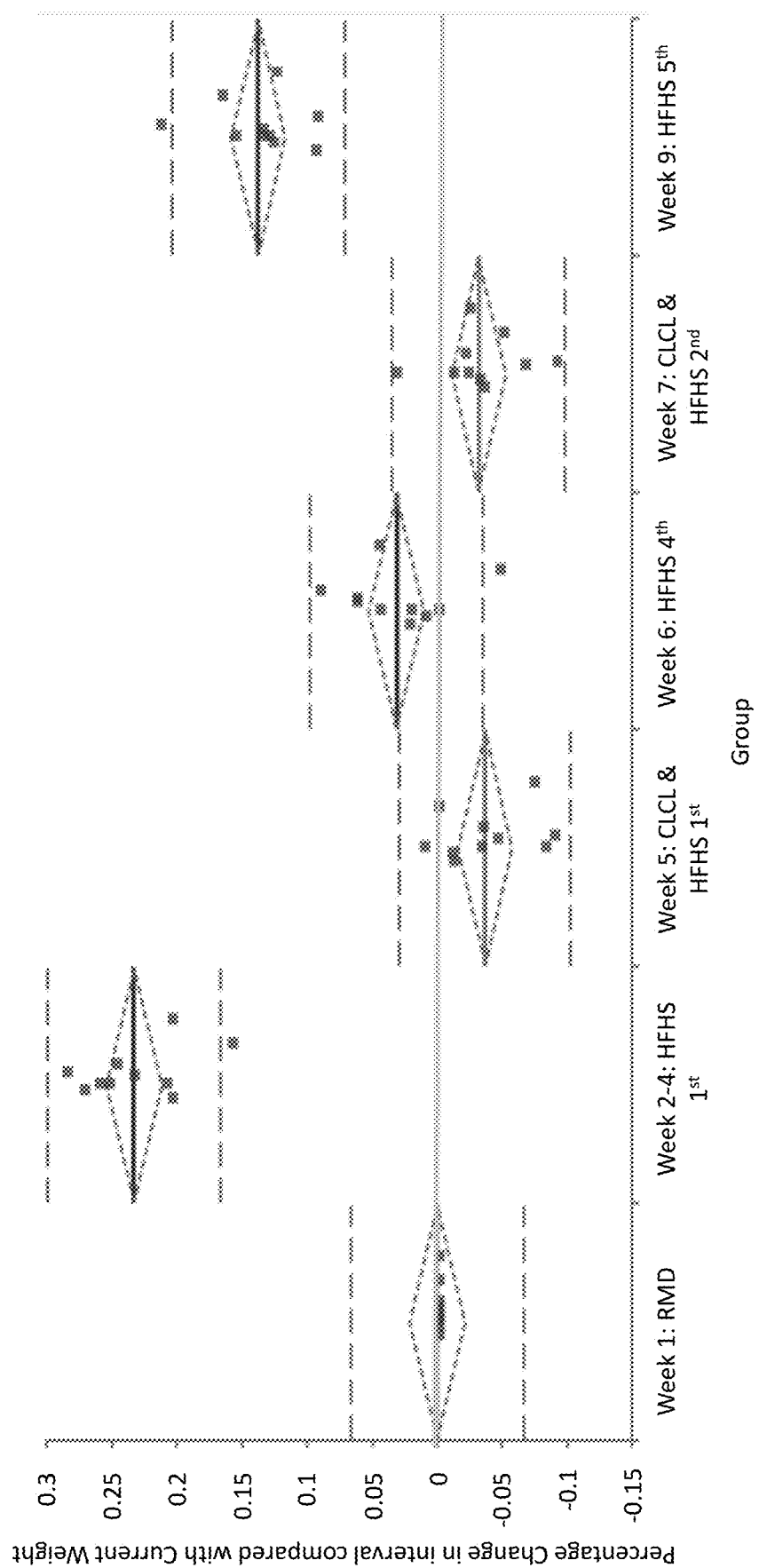
FIG. 6 is a graph showing the rate of weight gain in rats fed on CLC-enriched diet.
Figure 7:
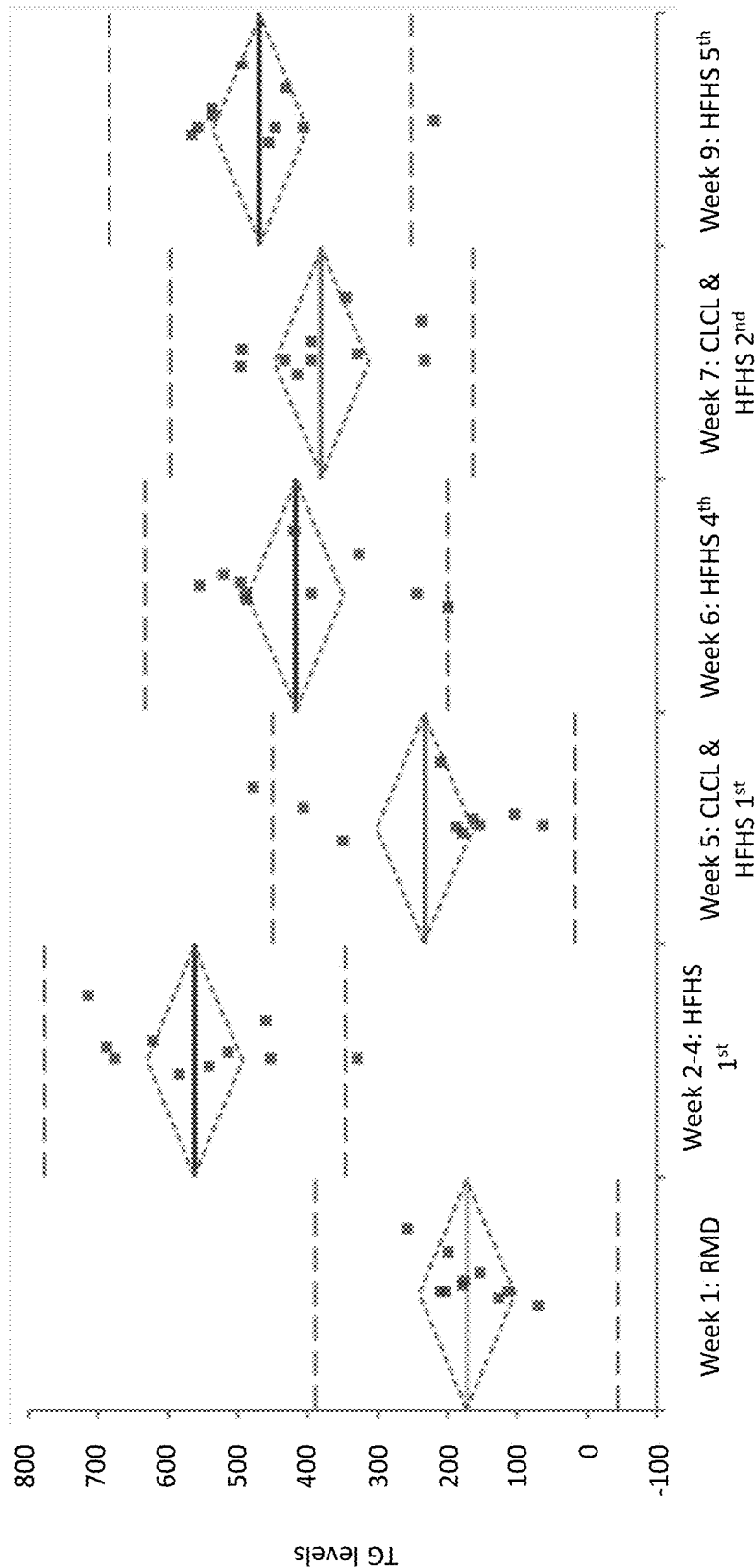
FIG. 7 is a graph showing the concentration of triglycerides in the blood of rats fed on of CLC-enriched diet. Blood was collected from unfasted animals.
Figure 8:
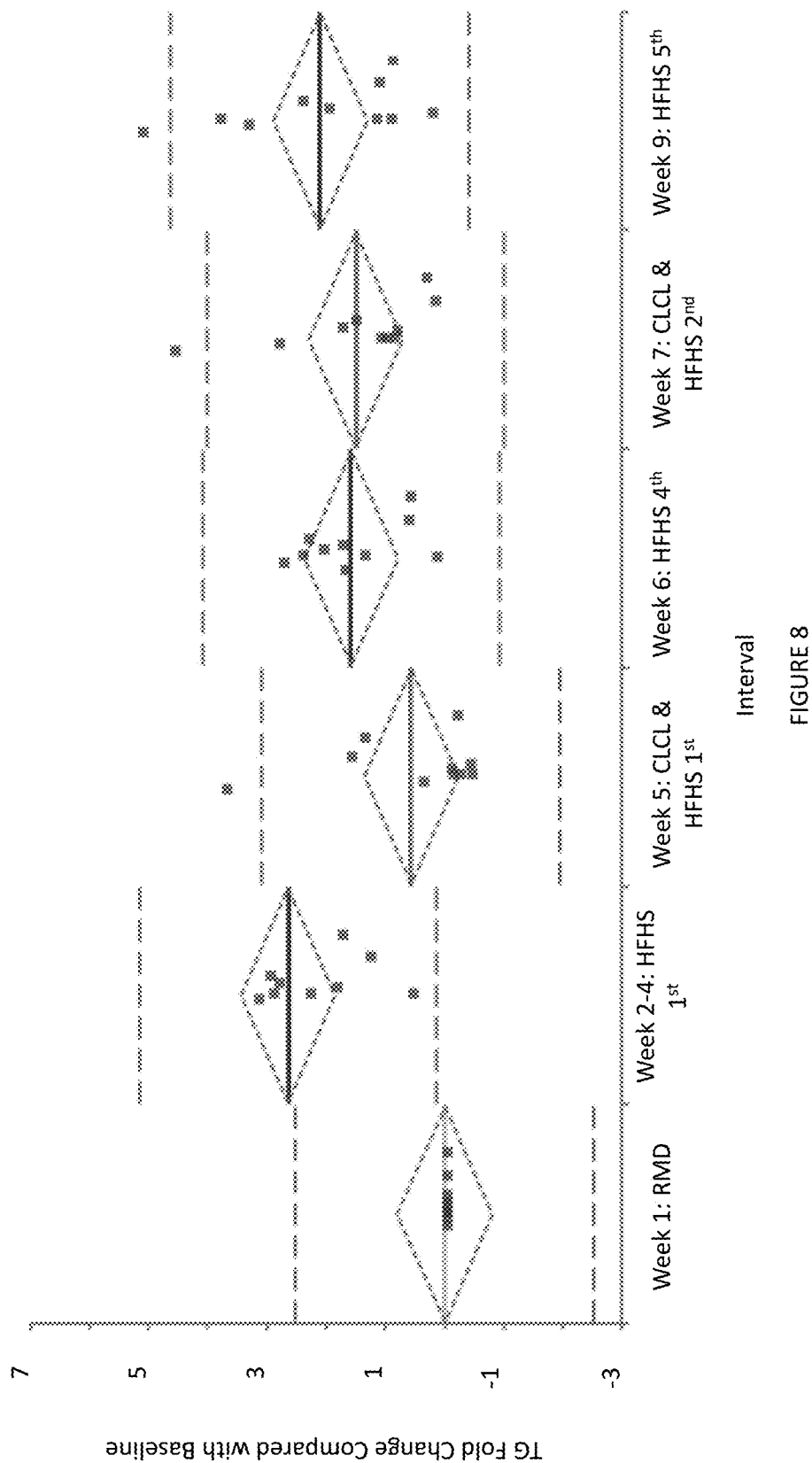
FIG. 8 is a graph showing fold change of triglycerides concentration in the blood of rats fed on of CLC-enriched diet. Blood was collected from unfasted animals.
Figure 9:
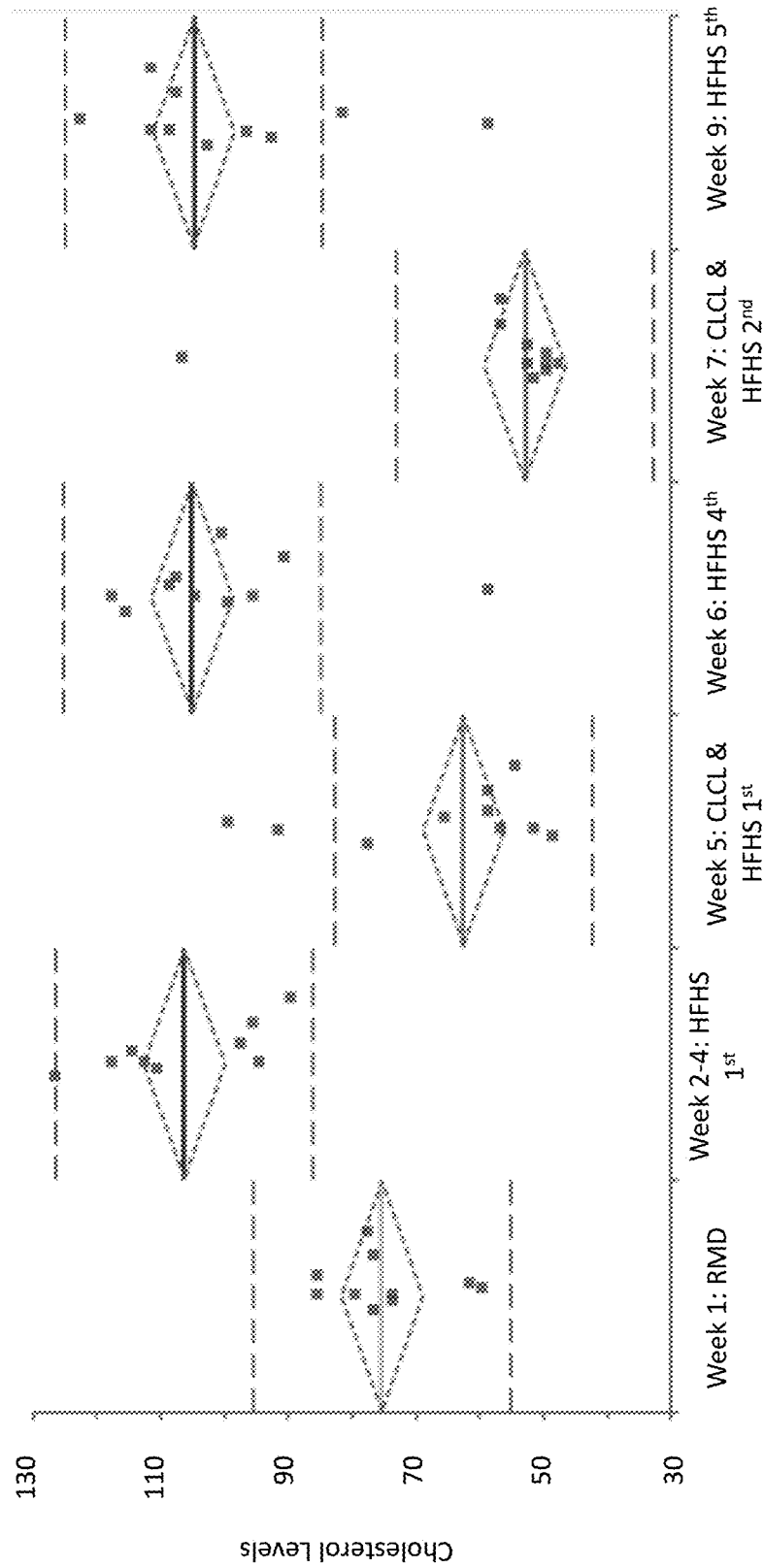
FIG. 9 is a graph showing the total cholesterol values in the blood of rats fed on of CLC-enriched diet. Blood was collected from unfasted animals.
Figure 10:
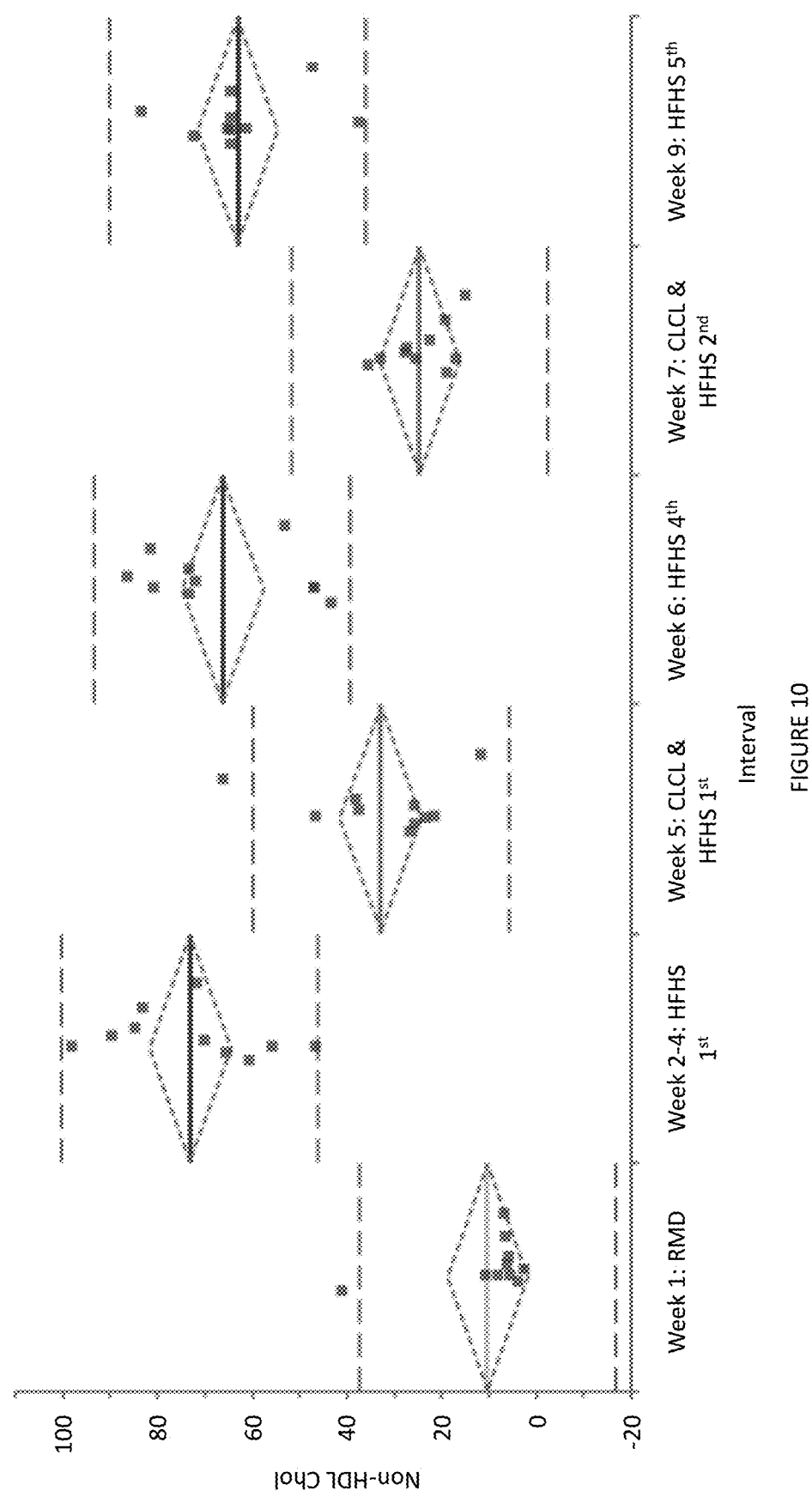
FIG. 10 is a graph showing the non-High density lipoprotein (HDL) cholesterol values in the blood of rats fed on of CLC-enriched diet. Blood was collected from unfasted animals.
Figure 11:
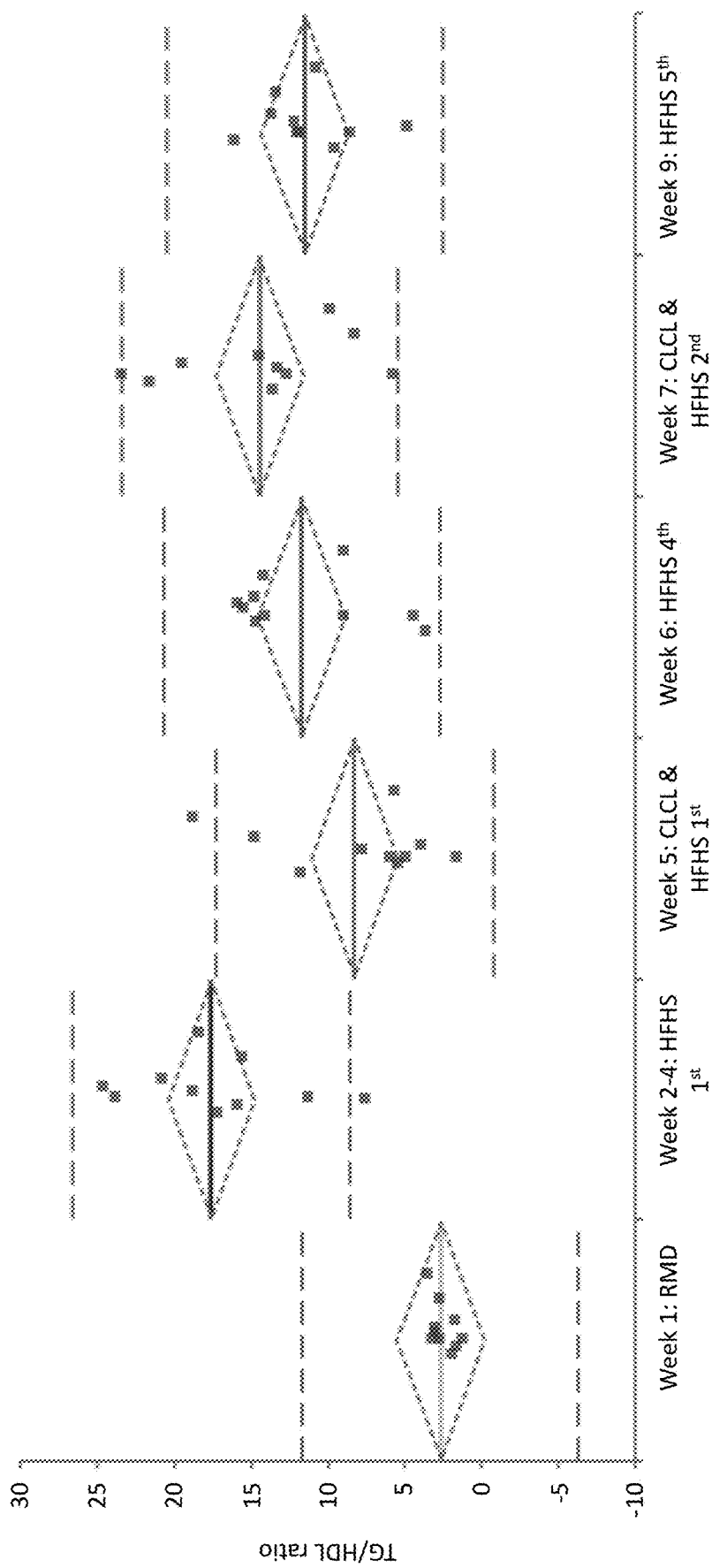
FIG. 11 is a graph showing the triglyceride to HDL ratio in the blood of rats fed on of CLC-enriched diet. Blood was collected from unfasted animals.

Moreover, as shown in FIG. 2 while the combination of CBD and chitosan group showed unexpected, and synergistic Triglycerides lowering effect, the differences between the CNTL and the CBD groups was not significant although the CBD group displayed lower TG values.

In conclusion, Body weight gain is inhibited by the CBD CHITOSAN therapy and the difference is significant between CHITOSAN and CNTL.

Blood chemistry values were basically the same for each parameter at the baseline sampling. CBD and CHITOSAN treatment led to a significant reduction in triglycerides. The decrease was synergistic as compared to the effect of CHITOSAN alone or CBD alone.

Example 2

Hypocholesterolemic Effects of Chitosan-Lecithin/Cbd Formulations in the Rat Dyslipidemia Model The objective of this study was to examine the blood cholesterol and triglycerides in male rats, following an oral administration of various formulations of the Test ties (specified hereinbelow) as administered in the diet in correlation to the HFHS diet alone.

The primary endpoint was the evaluation of the cholesterol lowering effect of CLC enriched diet. The secondary endpoints were the effects of CLC on triglyceride levels and on weight change during HFHS diet.

Materials and Methods
Formulation

| High Fat High Sugar Diet: | |
|---|---|
| Name: | Diet D110239 |
| Manufacturer: | TEKLAD, INC. |
| Chemical Name/Formulation: | See appendix I |
| Storage conditions: | Room Temperature |
| Expiry Date: | 2018 |
| Name to be used in the report: | Controlled diet |
| Date of receipt at test facility: | 28 Jun. 2017 |
| Purity to be stated in the report: | NA |
| Physical appearance (Test item): | Soft pellets |
| Name (formulated diet): | Fattening Diet |
| Physical appearance (formulated diet): | Pelleted diet |

| Test item 1: | |
|---|---|
| Name: | CBD Lecit0.7:1 Chitosan |
| CBD Manufacturer: | Scientific Health Solutions |
| Chemical Name/Formulation: | Cannabidiol and Chitosan-Lecithin particle |
| Storage conditions: | RT |
| Expiry Date: | NA |
| Name to be used in the report: | CLC |
| Date of receipt at test facility: | 23 Feb. 2018 |
| Purity to be stated in the report: | Not less than 99% |
| Physical appearance (Test item): | Blue putty |
| Name (formulated diet): | CBD-Chitosan |
| Physical appearance (formulated diet): | Bluish putty |

| Vehicle for CBD: | |
|---|---|
| Name | CBD:Olive Oil 2800 mg/10 ml vol |
| Manufacturer: | Sponsor |
| Chemical Name/Formulation: | Olive oil |
| Storage conditions: | RT |
| Expiry Date: | NA |
| Name to be used in the report: | oil |
| Date of receipt at test facility: | 23 Feb. 2018 |
| Purity to be stated in the report: | Absolute |
| Physical appearance (Test item): | Liquid |
| Name (formulated diet): | NA |
| Physical appearance (formulated diet): | NA |

Formulation of the Test Items:
Pelleted Diet

TEKLAD prepared a custom diet designed to induce elevation of cholesterol levels and induction of dyslipidemia in rodents. All diets were provided to the test facility as a ready to use pelleted diets, sterilized and vacuum packed. All aspects of the supplied Test Items, as to the required final concentrations in the ready pelleted diets, and all chemical/physical aspects of the diets were under the knowledge of the sponsor and authorized by him.

Chitosan Diet

Dose level 80 grams of Lechit0.7:1 chitosan/2 kg DietD110239.

Preparation of chitosan diet: 4 kg of DietD110239 were grounded into powder; 160 grams of Lecit0.7:1 L were added to 330 of tap water. The paste was thoroughly mixed. Desiccated for 48 hours in a vacuum desiccator at 25° C.

CBD Chitosan Diet

Dose level 1 gram CBD/2,000 g chitosan diet (15 mg CBD per 30 grams diet)

Preparation of CBD chitosan diet: 1,200 g chitosan diet were grounded into powder. 3 grams of CBD in 10 ml oil were added to 30 ml of tap water. The paste was thoroughly mixed. Desiccated for 48 hours in a vacuum desiccator at 25° C.

Animals

Wistar male rates with mean body weights of 330 g were used at study initiation. The minimum and maximum weights of the group did not exceed±20% of group mean body weight.

During acclimation animals were fed ad libitum "free-feeding" a commercial rodent maintenance diet (Harlan Teklad Diet cat #: 2914).

Study Initiation Definition

"Day 0" was initiation of the Study period, animals received RMD diet. Day 7 fattening diet was started after the animals were subjected to blood withdrawal and subsequently the first day of supplying the fattening diet. On day 22 HFHS & CLC diet was administered to the relevant group. On day 29 Fattening diet alone was provided until day 35. From day 36 to 42 d HFHS & CLC diet was administered. Then 14 days of fattening diet were administered.

Test Item Administration

The Test Item was divided into either: ready to use putty for the fattening diet, provided ad libitum; or ready to use putty for the CLC diet, provided ad libitum Body Weight Measurement Determination of individual body weights of animals was conducted once weekly during the entire study.

Blood Collection

Blood was collected six times during the study as follows: (1) Day 7 all animals RMD diet; (2) Day 21 all animals HFHS diet; (3) Day 29 all animals CLC & HFHS diet; (4) Day 35 all animals HFHS diet; (5) Day 42 all animals CLC & HFHS diet; and (6) Day 56 all animals HFHS diet.

The blood collection tubes (BD 367955) were specialized for serum separation, containing a clot activator and a gel which separates the cell content (pellet) from the serum (supernatant) after centrifugation. Blood samples of 0.5 mL/animal were collected into the pre marked tubes (study code, animal number and date). At all times blood was collected under anesthesia (Ketamine 20-40 mg/kg & Diazepam 1-2 mg/kg IM). Blood collection of all animals was performed via the periorbital eye venous plexus puncture.

Serum Preparation

Blood samples were left at room temperature for at least 45 minutes, and subsequently centrifuged (1790 g, 10 min/RT) for serum separation and left in the specialized tubes with the gel partitioning the separated serum and cell content. The samples were transferred as such to AML.

Blood Lipid Profile Determination

Following serum separation, the samples were kept at 2-8° C. until transferred to AML, for blood lipid profile analysis (cholesterol, LDL, HDL and Triglyceride levels). Samples transfer was via wet ice packed in Styrofoam boxes and transferred within 1-2 hours from blood separation.

Results

The differences in the weight parameters (comparative, rate of gain, etc.) between the CLC & HFHS diet and the HFHS diet were significant.

The CLC addition positively affected the weight gain seen during HFHS diet. The effect was similar to that of RMD diet (i.e. normalization of the weight change rate).

CLC therapy decreased the TG levels. During the first CLC interval the difference was significant. As blood tests were taken in unfasted animals, it is possible that the decrease in the second CLC interval was smaller due to temporal proximity to feeding.

The triglycerides were shown to increase about three-fold following instigation of HFHS diet. The decline in triglycerides levels was significant between the first CLC treatment and the induction phase (HFHS diet for 3 weeks) but not between the 2nd CLC treatment and the following interval.

The amount of non-HDL cholesterol is known to correlate with the incidence of cardiovascular events (Dharuni et al., 2016). CLC was found to decrease the amount of non-HDL cholesterol.

The first CLC therapy was found to decrease the Triglycerides to HDL ratio. However, the decrease in the $2^{nd}$ CLC interval was smaller, possibly due to a technical set-up (blood samples were taken in a fed or non-fasted state).

The inventors thus concluded that, under the conditions of the present study, that CLC reverses body weight gain tendency due to HFHS diet and decreases cholesterol levels by about 40 percent. Further, CLC therapy achieved a significant decrease of triglycerides levels.

TABLE 10A

Change of animals' weight during the study
N 80

| weight by group | N | Mean | 95% CI* | Mean SE* | SD |
|---|---|---|---|---|---|
| Week 1: RMD | 10 | 354.500 | 340.643 to 368.357 | 6.9510 | 8.317 |
| Week 2: HFHS $1^{st}$ | 10 | 365.500 | 351.643 to 379.357 | 6.9510 | 9.560 |
| Week 3: HFHS $2^{nd}$ | 10 | 426.500 | 412.643 to 440.357 | 6.9510 | 21.350 |
| Week 4: HFHS $3^{rd}$ | 10 | 463.000 | 449.143 to 476.857 | 6.9510 | 20.028 |
| Week 5: CLC & HFHS $1^{st}$ | 10 | 447.000 | 433.143 to 460.857 | 6.9510 | 21.756 |
| Week 6: HFHS $4^{th}$ | 10 | 462.000 | 448.143 to 475.857 | 6.9510 | 26.373 |
| Week 7: CLC & HFHS $2^{nd}$ | 10 | 448.000 | 434.143 to 461.857 | 6.9510 | 26.479 |
| Week 9: HFHS $5^{th}$ | 10 | 520.000 | 506.143 to 533.857 | 6.9510 | 31.981 |
| Pooled | 80 | | | | 21.981 |

*Standard error of the mean based on the pooled sample variance.

TABLE 10B

Statistical analysis
ANOVA

| Source | SS | DF | MS | F | p-value |
|---|---|---|---|---|---|
| group | 204284.688 | 7 | 29183.527 | 60.40 | <0.0001 |
| Error | 34787.500 | 72 | 483.160 | | |
| Total | 239072.188 | 79 | 3026.230 | | |

H0: $\mu_1 = \mu_2 = \mu \ldots$
The means of the populations are all equal.
H1: $\mu_i \neq \mu_j$ for at least one i, j
The means of the populations are not all equal.

TABLE 11A

Change of animals' weight compared to basal weight during the study
N 80

| Change in Weight compared to Baseline by group | N | Mean | 95% CI* | Mean SE* | SD |
|---|---|---|---|---|---|
| Week 1: RMD | 10 | 0.000 | −14.406 to 14.406 | 7.2267 | 0.000 |
| Week 2: HFHS 1st | 10 | 11.000 | −3.406 to 25.406 | 7.2267 | 7.379 |
| Week 3: HFHS 2nd | 10 | 72.000 | 57.594 to 86.406 | 7.2267 | 20.028 |
| Week 4: HFHS 3rd | 10 | 108.500 | 94.094 to 122.906 | 7.2267 | 21.991 |
| Week 5: CLC & HFHS 1st | 10 | 92.500 | 78.094 to 106.906 | 7.2267 | 19.472 |
| Week 6: HFHS 4th | 10 | 107.500 | 93.094 to 121.906 | 7.2267 | 28.013 |
| Week 7: CLC & HFHS 2nd | 10 | 93.500 | 79.094 to 107.906 | 7.2267 | 29.912 |
| Week 9: HFHS 5th | 10 | 165.500 | 151.094 to 179.906 | 7.2267 | 34.355 |
| Pooled | 80 | | | | 22.853 |

*Standard error of the mean based on the pooled sample variance.

TABLE 11B

Statistical analysis
ANOVA

| Source | SS | DF | MS | F | p-value |
|---|---|---|---|---|---|
| group | 204284.688 | 7 | 29183.527 | 55.88 | <0.0001 |
| Error | 37602.500 | 72 | 522.257 | | |
| Total | 241887.188 | 79 | 3061.863 | | |

H0: $\mu_1 = \mu_2 = \mu \ldots$
The means of the populations are all equal.
H1: $\mu_i \neq \mu_j$ for at least one i, j
The means of the populations are not all equal.

TABLE 12A

Change in animals' rate of weight gain compared with previous interval
N 60

| Percentage Change per Interval compared with Current Weight by group | N | Mean | 95% CI* | Mean SE* | SD |
|---|---|---|---|---|---|
| Week 1: RMD | 10 | 0.000 | −0.021 to 0.021 | 0.0105 | 0.000 |
| Week 2-4: HFHS 1st | 10 | 0.233 | 0.212 to 0.254 | 0.0105 | 0.039 |
| Week 5: CLC & HFHS 1st | 10 | −0.037 | −0.058 to −0.016 | 0.0105 | 0.035 |
| Week 6: HFHS 4th | 10 | 0.031 | 0.010 to 0.052 | 0.0105 | 0.039 |
| Week 7: CLC & HFHS 2nd | 10 | −0.032 | −0.053 to −0.011 | 0.0105 | 0.033 |
| Week 9: HFHS 5th | 10 | 0.138 | 0.117 to 0.159 | 0.0105 | 0.033 |
| Pooled | 60 | | | | 0.033 |

*Standard error of the mean based on the pooled sample variance.

Table 12B – Statistical analysis

ANOVA

| Source | SS | DF | MS | F | p-value |
|---|---|---|---|---|---|
| group | 0.580 | 5 | 0.116 | 105.51 | <0.0001 |
| Error | 0.059 | 54 | 0.001 | | |
| Total | 0.640 | 59 | 0.011 | | |

H0: $\mu_1 = \mu_2 = \mu...$
The means of the populations are all equal.
H1: $\mu_i \neq \mu_j$ for at least one i,j
The means of the populations are not all equal.

Multiple Comparisons

Tukey-Kramer all pairs comparisons

| Contrast | Mean difference | Simultaneous 95% CI | SE | 0 | p-value |
|---|---|---|---|---|---|
| Week 2-4:HFHS 1st – Week 5: CLC&HFHS 1st | 0.270 | 0.026 to 0.313 | 0.0148 | | <0.0001[1] |
| Week 2-4:HFHS 1st – Week 7: CLC&HFHS 2nd | 0.265 | 0.221 to 0.309 | 0.0148 | | <0.0001[1] |
| Week 2-4:HFHS 1st – Week 1: RMD | 0.233 | 0.189 to 0.277 | 0.0148 | | <0.0001[1] |
| Week 2-4:HFHS 1st – Week 6: HFHS 4th | 0.202 | 0.158 to 0.245 | 0.0148 | | <0.0001[1] |
| Week 9:HFHS 5th – Week 5: CLC&HFHS 1st | 0.174 | 0.130 to 0.218 | 0.0148 | | <0.0001[1] |
| Week 9:HFHS 5th – Week 7: CLC&HFHS 2nd | 0.170 | 0.126 to 0.213 | 0.0148 | | <0.0001[1] |
| Week 9:HFHS 5th – Week 1:RMD | 0.138 | 0.094 to 0.182 | 0.0148 | | <0.0001[1] |
| Week 9:HFHS 5th – Week 6: HFHS 4th | 0.106 | 0.063 to 0.150 | 0.0148 | | <0.0001[1] |

| | | | | | |
|---|---|---|---|---|---|
| Week 2-4:HFHS 1st – Week 9: HFHS 5th | 0.095 | 0.051 to 0.139 | 0.0148 | | <0.0001[1] |
| Week 6:HFHS 4th – Week 5: CLC&HFHS 1st | 0.068 | 0.024 to 0.112 | 0.0148 | | <0.0004[1] |
| Week 6:HFHS 4th – Week: CLC&HFHS 2nd | 0.063 | 0.019 to 0.107 | 0.0148 | | <0.0011[1] |
| Week 1:RMD – Week 5: CLC&HFHS 1st | 0.037 | -0.007 to 0.080 | 0.0148 | | 0.1531[2] |
| Week 1:RMD – Week 7: CLC&HFHS 2nd | 0.032 | -0.012 to 0.076 | 0.0148 | | 0.2795[2] |
| Week 6:HFHS 4th – Week 1:RMD | 0.031 | -0.012 to 0.075 | 0.0148 | | 0.2958[2] |
| Week 7: CLC&HFHS 2nd – Week 5: CLC&HFHS 1st | 0.005 | -0.039 to 0.049 | 0.0148 | | 0.9995[2] |

H0: Θ=0
The difference between the means of the population is equal to 0.
H1: Θ≠0
The difference between the means if the populations is equal to 0.
[1] Reject the null hypothesis in favor of the alternative hypothesis at the 5% significance level.
[2] Do not reject the null hypothesis at the 5% significance level.

Table 13A – Triglycerides levels

| N | 60 |
|---|---|

| TG Levels by Interval | N | Mean | 95% CI* | Mean SE* | SD |
|---|---|---|---|---|---|
| Week 1: RMD | 10 | 172.9 | 104.3 to 241.5 | 34.19 | 54.2 |
| Week 2-4: HFHS 1st | 10 | 562.1 | 493.5 to 630.7 | 34.19 | 122.5 |
| Week 5: CLC & HFHS 1st | 10 | 233.2 | 164.6 to 301.8 | 34.19 | 135.7 |
| Week 6: HFHS 4th | 10 | 417.0 | 348.4 to 485.6 | 34.19 | 121.2 |
| Week 7: CLC & HFHS 2nd | 10 | 380.6 | 312.0 to 449.2 | 34.19 | 92.3 |
| Week 9: HFHS 5th | 10 | 468.7 | 400.1 to 537.3 | 34.19 | 102.8 |
| Pooled | 60 | | | | 108.1 |

* Standard error of the mean based on the pooled sample variance.

Table 13B – Statistical analysis

ANOVA

| Source | SS | DF | MS | F | p-value |
|---|---|---|---|---|---|
| Interval | 1064930.7 | 5 | 212986.1 | 18.22 | <0.0001 |
| Error | 631369.9 | 54 | 11692.0 | | |
| Total | 1696300.6 | 59 | 28750.9 | | |

H0: $\mu_1 = \mu_2 = \mu$...

The means of the populations are all equal.

H1: $\mu_i \neq \mu_j$ for at least one i,j

The means of the populations are not all equal.

Multiple Comparisons

Tukey-Kramer all pairs comparisons

| Contrast | Mean difference | Simultaneous 95% CI | SE | 0 | p-value |
|---|---|---|---|---|---|
| Week 2-4:HFHS $1^{st}$ – Week 1: RMD | 389.2 | 246.3 to 532.1 | 48.36 | | <0.0001[1] |
| Week 2-4:HFHS $1^{st}$ – Week 5: CLC&HFHS $1^{st}$ | 328.9 | 186.0 to 471.8 | 48.36 | | <0.0001[1] |
| Week 9:HFHS $5^{th}$ – Week 1: RMD | 295.8 | 152.9 to 438.7 | 48.36 | | <0.0001[1] |
| Week 6:HFHS $4^{th}$ – Week 1:RMD | 244.1 | 101.2 to 387.0 | 48.36 | | <0.0001[1] |
| Week 9:HFHS $5^{th}$ – Week 5: CLC&HFHS $1^{st}$ | 235.5 | 92.6 to 378.4 | 48.36 | | <0.0001[1] |
| Week 7: CLC&HFHS $2^{nd}$ – Week 1:RMD | 207.7 | 64.8 to 350.6 | 48.36 | | <0.0010[1] |
| Week 6:HFHS $4^{th}$ – Week 5: CLC&HFHS $1^{st}$ | 183.8 | 40.9 to 326.7 | 48.36 | | <0.0047[1] |
| Week 2-4:HFHS $1^{st}$ – Week 7: HFHS $2^{nd}$ | 181.5 | 38.6 to 324.4 | 48.36 | | <0.0055[1] |
| Week 7: CLC&HFHS | 147.4 | 4.5 to 290.3 | 48.36 | | <0.0394[1] |

| Comparison | Mean | 95% CI | SE | | p-value |
|---|---|---|---|---|---|
| 2nd − Week 5: CLC&HFHS 1st Week 2-4:HFHS 1st − Week 6:HFHS 4th | 145.1 | 2.2 to 288.0 | 48.36 |  | <0.0445[1] |
| Week 2-4:HFHS 1st − Week 9:HFHS 5th | 93.4 | −49.5 to 236.3 | 48.36 |  | <0.3948[2] |
| Week 9:HFHS 5th − Week 7: CLC&HFHS 2nd | 88.1 | −54.8 to 231.0 | 48.36 |  | 0.4608[2] |
| Week 5:CLC&HFHS 1st − Week 1:RMD | 60.3 | −82.6 to 203.2 | 48.36 |  | 0.8117[2] |
| Week 9:HFHS 5th − Week 6: HFHS 4th | 51.7 | −91.2 to 194.6 | 48.36 |  | 0.8914[2] |
| Week 6:HFHS 4th − Week 7:CLC&HFHS 2nd | 36.4 | −106.5 to 179.3 | 48.36 |  | 0.9741[2] |

H0: Θ=0
The difference between the means of the population is equal to 0.
H1: Θ≠0
The difference between the means if the populations is equal to 0.
[1] Reject the null hypothesis in favor of the alternative hypothesis at the 5% significance level.
[2] Do not reject the null hypothesis at the 5% significance level.

Table 14A − Total cholesterol levels

| Cholesterol Levels by Interval | N | Mean | 95% CI* | Mean SE* | SD |
|---|---|---|---|---|---|
| Week 1: RMD | 10 | 75.4 | 69.0 to 81.8 | 3.19 | 8.7 |
| Week 2-4: HFHS 1st | 10 | 106.3 | 99.9 to 112.7 | 3.19 | 12.1 |
| Week 5: CLC & HFHS 1st | 10 | 62.6 | 56.2 to 69.0 | 3.19 | 13.1 |
| Week 6: HFHS 4th | 10 | 105.1 | 98.7 to 111.5 | 3.19 | 8.4 |
| Week 7: CLC & HFHS 2nd | 10 | 52.9 | 46.5 to 59.3 | 3.19 | 3.7 |
| Week 9: HFHS 5th | 10 | 104.7 | 98.3 to 111.1 | 3.19 | 11.5 |
| Pooled | 60 | | | | 10.1 |

* Standard error of the mean based on the pooled sample variance.

Table 14B – Statistical analysis

ANOVA

| Source | SS | DF | MS | F | p-value |
|---|---|---|---|---|---|
| Interval | 28686.2 | 5 | 5737.2 | 56.46 | <0.0001 |
| Error | 5486.8 | 54 | 101.6 | | |
| Total | 34173.0 | 59 | 579.2 | | |

H0: $\mu_1 = \mu_2 = \mu$...
The means of the populations are all equal.
H1: $\mu_i \neq \mu_j$ for at least one i,j
The means of the populations are not all equal.

Multiple Comparisons

Tukey-Kramer all pairs comparisons

| Contrast | Mean difference | Simultaneous 95% CI | SE | 0 | p-value |
|---|---|---|---|---|---|
| Week 2-4:HFHS $1^{st}$ – Week 7: CLC&HFHS $2^{nd}$ | 53.4 | 40.1 to 66.7 | 4.51 | | <0.0001[1] |
| Week 6:HFHS $4^{th}$ – Week 7: CLC&HFHS $2^{nd}$ | 52.2 | 38.9 to 65.5 | 4.51 | | <0.0001[1] |
| Week 9:HFHS $5^{th}$ – Week 7: CLC&HFHS $2^{nd}$ | 51.8 | 38.5 to 65.1 | 4.51 | | <0.0001[1] |
| Week 2-4:HFHS $1^{st}$ – Week 5: CLC&HFHS $1^{st}$ | 43.7 | 30.4 to 57.0 | 4.51 | | <0.0001[1] |
| Week 6:HFHS $4^{th}$ – Week 5: CLC&HFHS $1^{st}$ | 42.5 | 29.2 to 55.8 | 4.51 | | <0.0001[1] |
| Week 9:HFHS $5^{th}$ – Week 5: CLC&HFHS $1^{st}$ | 42.1 | 28.8 to 55.4 | 4.51 | | <0.0001[1] |
| Week 2-4:HFHS $1^{st}$ – Week 1:RMD | 30.9 | 17.6 to 44.2 | 4.51 | | <0.0001[1] |

| | | | | | |
|---|---|---|---|---|---|
| Week 6:HFHS 4th – Week 1:RMD | 29.7 | 16.4 to 43.0 | 4.51 | | <0.0001[1] |
| Week 9:HFHS 5th – Week 1:RMD | 29.3 | 16.0 to 42.6 | 4.51 | | <0.0001[1] |
| Week 1:RMD – Week 7: CLC&HFHS 2nd | 22.5 | 9.2 to 35.8 | 4.51 | | <0.0001[1] |
| Week 1:RMD – Week 5: CLC&HFHS 1st | 12.8 | 0.5 to 26.1 | 4.51 | | <0.0063[2] |
| Week 5: CLC&HFHS 1st – Week 7: CLC&HFHS 2nd | 9.7 | 3.6 to 23.0 | 4.51 | | 0.2773[2] |
| Week 2-4:HFHS 1st – Week 9:HFHS 5th | 1.6 | 11.7 to 14.9 | 4.51 | | 0.9992[2] |
| Week 2-4:HFHS 1st – Week 6:HFHS 4th | 1.2 | 12.1 to 14.5 | 4.51 | | 0.9998[2] |
| Week 6:HFHS 4th – Week 9:HFHS 5th | 0.4 | 12.9 to 13.7 | 4.51 | | 1.0000[2] |

H0: Θ=0
The difference between the means of the population is equal to 0.
H1: Θ≠0
The difference between the means if the populations is equal to 0.
[1] Reject the null hypothesis in favor of the alternative hypothesis at the 5% significance level.
[2] Do not reject the null hypothesis at the 5% significance level.

Table 15A – Non-HDL cholesterol levels

| Non HDL Cholesterol by Interval | N | Mean | 95% CI* | Mean SE* | SD |
|---|---|---|---|---|---|
| Week 1: RMD | 10 | 10.34 | 1.75 to 18.93 | 4.283 | 11.21 |
| Week 2-4: HFHS 1st | 10 | 73.09 | 64.50 to 81.68 | 4.283 | 16.22 |
| Week 5: CLC & HFHS 1st | 10 | 32.90 | 24.31 to 41.49 | 4.283 | 15.38 |
| Week 6: HFHS 4th | 10 | 66.29 | 57.70 to 74.88 | 4.283 | 16.44 |
| Week 7: CLC & HFHS 2nd | 10 | 24.68 | 16.09 to 33.27 | 4.283 | 6.83 |
| Week 9: HFHS 5th | 10 | 63.06 | 54.47 to 71.65 | 4.283 | 12.60 |
| Pooled | 60 | | | | 13.55 |

* Standard error of the mean based on the pooled sample variance.

Table 15B – Statistical analysis

ANOVA

| Source | SS | DF | MS | F | p-value |
|---|---|---|---|---|---|
| Interval | 33290.82 | 5 | | 36.29 | <0.0001 |
| Error | 9907.92 | 54 | | | |
| Total | 43198.74 | 59 | | | |

H0: $\mu_1 = \mu_2 = \mu$...
The means of the populations are all equal.
H1: $\mu_i \neq \mu_j$ for at least one i,j
The means of the populations are not all equal.

Multiple Comparisons

Tukey-Kramer all pairs comparisons

| Contrast | Mean difference | Simultaneous 95% CI | SE | 0 | p-value |
|---|---|---|---|---|---|
| Week 2-4:HFHS 1$^{st}$ – Week 1: RMD | 62.75 | 44.85 to 80.65 | 6.058 | □ | <0.0001[1] |
| Week 6: HFHS 4$^{th}$ – Week 1: RMD | 55.95 | 38.05 to 73.85 | 6.058 | □ | <0.0001[1] |
| Week 9: HFHS 5$^{th}$ – Week 1: RMD | 52.72 | 34.82 to 70.62 | 6.058 | □ | <0.0001[1] |
| Week 2-4:HFHS 1$^{st}$ – Week 7: CLC&HFHS 2$^{nd}$ | 48.41 | 30.51 to 66.31 | 6.058 | □ | <0.0001[1] |
| Week 6:HFHS 4$^{th}$ – Week 7: CLC&HFHS 2$^{nd}$ | 41.61 | 23.71 to 59.51 | 6.058 | □ | <0.0001[1] |
| Week 2-4:HFHS 1$^{st}$ – Week 5 CLC&HFHS 1$^{st}$ | 40.19 | 22.29 to 58.09 | 6.058 | □ | <0.0001[1] |
| Week 9: HFHS 5$^{th}$ – Week 7: CLC&HFHS 2$^{nd}$ | 38.38 | 20.48 to 56.28 | 6.058 | □ | <0.0001[1] |
| Week 6: HFHS 4$^{th}$ – Week 5 | 33.39 | 15.49 to 51.29 | 6.058 | □ | <0.0001[1] |

| | | | | | |
|---|---|---|---|---|---|
| CLC&HFHS 1st Week 9: HFHS 5th – Week 5 CLC&HFHS 1st | 30.16 | 12.26 to 48.05 | 6.058 | | <0.0001[1] |
| Week 5 CLC&HFHS 1st – Week 1: RMD | 22.56 | 4.66 to 40.46 | 6.058 | | <0.0060[1] |
| Week 7 CLC&HFHS 2nd – Week 1: RMD | 14.34 | -3.56 to 32.24 | 6.058 | | <0.1862[2] |
| Week 2-4:HFHS 1st – Week 9 :HFHS 5th | 10.03 | -7.87 to 27.93 | 6.058 | | 0.5662[2] |
| Week 5 CLC&HFHS 1st – Week 7 CLC&HFHS 2nd | 8.22 | -9.68 to 26.12 | 6.058 | | 0.7519[2] |
| Week 2-4:HFHS 1st – Week 6: HFHS 4th | 6.80 | -11.10 to 24.70 | 6.058 | | 0.8699[2] |
| Week 6: HFHS 4th – Week 9 :HFHS 5th | 3.23 | -14.67 to 21.13 | 6.058 | | 0.9946[2] |

H0: Θ=0

The difference between the means of the population is equal to 0.

H1: Θ≠0

The difference between the means if the populations is equal to 0.

[1] Reject the null hypothesis in favor of the alternative hypothesis at the 5% significance level.

[2] Do not reject the null hypothesis at the 5% significance level.

Table 16A – Triglycerides to HDL ratio

| TG to HDL ratio by Interval | N | Mean | 95% CI* | Mean SE* | SD |
|---|---|---|---|---|---|
| Week 1: RMD | 10 | 2.686142476 | -0.158613651 to 5.530898603 | 1.418916412 | 0.760945293 |
| Week 2-4: HFHS 1st | 10 | 17.575770238 | 14.731014111 to 20.420526365 | 1.418916412 | 5.246380963 |
| Week 5: CLC & HFHS 1st | 10 | 8.252866979 | 5.408110852 to 11.097623106 | 1.418916412 | 5.358604168 |
| Week 6: HFHS 4th | 10 | 11.696459876 | 8.851703749 to 14.541216002 | 1.418916412 | 4.635133777 |

| | | | | | |
|---|---|---|---|---|---|
| Week 7: CLC & HFHS 2nd | 10 | 14.442527726 | 11.597771599 to 17.287283853 | 1.418916412 | 5.736595019 |
| Week 9: HFHS 5th | 10 | 11.489237558 | 8.644481431 to 14.333993684 | 1.418916412 | 3.096489947 |
| Pooled | 60 | | | | 4.487007673 |

* Standard error of the mean based on the pooled sample variance.

Table 16B – Statistical analysis

ANOVA

| Source | SS | DF | MS | F | p-value |
|---|---|---|---|---|---|
| Interval | $1.324797\ E^{+03}$ | 5 | $2.649594\ E^{+02}$ | 13.16 | <0.0001 |
| Error | $1.087195\ E^{+03}$ | 54 | 20.133237853 | | |
| Total | $2.411992\ E^{+03}$ | 59 | 40.881220997 | | |

H0: $\mu_1 = \mu_2 = \mu\ldots$
The means of the populations are all equal.
H1: $\mu_i \neq \mu_j$ for at least one i,j
The means of the populations are not all equal.

Multiple Comparisons

Tukey-Kramer all pairs comparisons

| Contrast | Mean difference | Simultaneous 95% CI | SE | 0 | p-value |
|---|---|---|---|---|---|
| Week 2-4:HFHS 1st – Week 1: RMD | 14.889627762 | 8.961017573 to 20.818237950 | 2.006650834 | | <0.0001[1] |
| Week 7: CLC&HFHS 2nd – Week 1: RMD | 11.756385250 | 5.827775061 to 17.684995438 | 2.006650834 | | <0.0001[1] |
| Week 2-4:HFHS 1st – Week 5 CLC&HFHS 1st | 9.322903259 | 3.394293071 to 15.251513447 | 2.006650834 | | 0.0003[1] |
| Week 6: HFHS 4th – Week 1: RMD | 9.010317399 | 3.081707211 to 14.938927588 | 2.006650834 | | 0.0005[1] |
| Week 9: HFHS 5th – Week 1: RMD | 8.803095081 | 2.874484893 to 14.731705270 | 2.006650834 | | 0.0007[1] |
| Week 7 CLC&HFHS 2nd – Week 5 CLC&HFHS 1st | 6.189660747 | 0.261050559 to 12.118270935 | 2.006650834 | | 0.0359[1] |

| | | | | | |
|---|---|---|---|---|---|
| Week 2-4:HFHS 1st – Week 9:HFHS 5th | 6.086532680 | 0.157922492 to 12.015142869 | 2.006650834 | | 0.0410[1] |
| Week 2-4:HFHS 1st – Week 6: HFHS 4th | 5.879310362 | -0.049299826 to 11.807920551 | 2.006650834 | | 0.0531[2] |
| Week 5 CLC&HFHS 1st – Week 1: RMD | 5.566724503 | -0.361885685 to 11.495334691 | 2.006650834 | | 0.0774[2] |
| Week 6: HFHS 4th – Week 5 CLC&HFHS 1st | 3.443592897 | -2.485017292 to 9.372203085 | 2.006650834 | | 0.5275[2] |
| Week 9: HFHS 5th – Week 5 CLC&HFHS 1st | 3.236370579 | -2.692239610 to 9.164980767 | 2.006650834 | | 0.5939[2] |
| Week 2-4:HFHS 1st – Week 7: CLC&HFHS 2nd | 3.133242512 | -2.795367676 to 9.164980767 | 2.006650834 | | 0.6268[2] |
| Week 7 CLC&HFHS 2nd – Week 9:HFHS 5th | 2.953290168 | -2.975320020 to 8.881900357 | 2.006650834 | | 0.6833[2] |
| Week 7 CLC&HFHS 2nd – Week 6:HFHS 4th | 2.746067850 | -3.182542338 to 8.674678039 | 2.006650834 | | 0.7453[2] |
| Week 6: HFHS 4th – Week 9: HFHS 5th | 0.207222318 | -5.721387870 to 6.135832506 | 2.006650834 | | 1.0000[2] |

H0: Θ=0
The difference between the means of the population is equal to 0.
H1: Θ≠0
The difference between the means if the populations is equal to 0.
[1] Reject the null hypothesis in favor of the alternative hypothesis at the 5% significance level.
[2] Do not reject the null hypothesis at the 5% significance level.

While certain features of the invention have been described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A composition comprising: (a) cannabidiol (CBD) and (b) chitosan, wherein the weight ratio between CBD and chitosan is 1:5 to 1:80.

2. The composition of claim 1, further comprising an anionic surfactant, a non-ionic surfactant, or a combination thereof.

3. The composition of claim 1, further comprising lecithin, a fatty alcohol, or a combination thereof.

4. The composition of claim 1, in the form of a composite particle.

5. The composition of claim 4, wherein said composite particle comprises an anionic surfactant, a non-ionic surfactant, or a combination thereof chemically bound to both said chitosan and said CBD.

6. The composition of claim 1, comprising: 50 to 600 mg CBD.

7. The composition of claim 2, wherein the weight ratio between: (a) said anionic surfactant, said non-ionic surfactant, or said combination thereof; and (b) chitosan; and (c) CBD is from 90:30:1 to 6:2:1 or from 2:1:0.1 to 0.5:1:0.1.

8. The composition of claim 1, further comprising Tetrahydrocannabinol (THC).

9. The composition of claim 1, further comprising THC in a CBD/THC w/w ratio of 40:1 to 2:1.

10. The composition of claim 1, further comprising: CBC, CBG, CBN or any combination thereof.

11. The composition of claim 1, wherein said composition is an oral composition, a systemic composition, a topical composition, a rectal composition, a transmucosal composition, a transnasal composition, an intestinal composition or a parenteral composition.

* * * * *